United States Patent [19]
Finot et al.

[11] Patent Number: 5,847,283
[45] Date of Patent: Dec. 8, 1998

[54] METHOD AND APPARATUS FOR THE EVALUATION OF A DEPTH PROFILE OF THERMO-MECHANICAL PROPERTIES OF LAYERED AND GRADED MATERIALS AND COATINGS

[75] Inventors: Marc Finot, Somerville; Olivera Kesler, Cambridge; Subra Suresh, Wellesley, all of Mass.

[73] Assignee: Massachusetts Institute of Technology, Cambridge, Mass.

[21] Appl. No.: 675,121

[22] Filed: Jul. 3, 1996

[51] Int. Cl.⁶ ........................................................ G01L 1/24
[52] U.S. Cl. ................................................ 73/812; 73/800
[58] Field of Search .............................. 73/788, 789, 800, 73/812, 849, 852

[56] References Cited

U.S. PATENT DOCUMENTS

| | | | |
|---|---|---|---|
| 4,912,355 | 3/1990 | Noel et al. | 73/800 |
| 5,044,205 | 9/1991 | Wolff et al. | 73/800 |
| 5,361,638 | 11/1994 | Pettersson et al. | 73/800 |
| 5,546,811 | 8/1996 | Rogers et al. | 73/800 |

OTHER PUBLICATIONS

T.F. Retajczyk, Jr. and A.K. Sinha, "Elastic Stiffness and Thermal Expansion Coefficient of BN Films", (Jan. 15, 1980), pp. 161–163, Apply. Phys. Lett., vol. 36, No. 2.

Cynthia G. Madras, et al., "Measurement of the Effect of Temperature on Stress Distribution and Deformation in Multilayer Optical Thin Film Structures", (1995), pp. 351–356, Mat. Res. Soc. Symp. Proc. vol. 356.

Jwo–Huei Jou, et al., "A Method for the Determination of Gold Thin Film's Mechanical Properties", (1994), pp. 70–72, Thin Solid Films, vol. 238.

M. Laugier, "Determination of Young's Modulus in Vacuum–Evaporated Thin Films of Aluminum and Silver", (1981), pp. L17–L18, Thin Solid Films, vol. 75.

Peter Alpern, et al., "Thermomechanical Assessment of Plastic Coated TAB Chips", (Oct. 1992) pp. 748–753, IEEE Transactions on Components, Hybrids and Manufacturing Technology, vol. 15, No. 5.

Hiroaki Asada, et al., "Measurement of Young's Moduli of TiC–Coated Film by the X–ray Method", (Dec. 15, 1993), pp. 247–252, Thin Solid Films, vol. 236, Nos. 1/2.

Chin–Chen Chiu, "Residual stresses in ceramic coatings as determined from the curvature of a coated strip", Materials Science and Engineering, A150 (1992), pp. 139–148.

R. Elsing et al., "Calculation of Residual Thermal Stress in Plasma–Sprayed Coatings", Surface and Coatings Technology, 43/44 (1990) pp. 416–425.

Seiji Kuroda, "Stress Generation in Plasma–Sprayed Coatings and its Correlation with the Deposit Microstructure", Colloquium Series, Mar. 29, 1996.

S.C. Gill et al., "Stress Distributions and Material Response in Thermal Spraying of Metallic and Ceramic Deposits", Metallurgical Transactions B, vol. 21B, Apr., 1990, pp. 377–385.

S.J. Howard et al., "The Effect of Residual Stresses on the Debonding of Coatings Under an Applied Load", Proceedings on the 7th National Thermal Spray Conference 20–24, Jun., 1994, pp. 703–708.

(List continued on next page.)

*Primary Examiner*—Max H. Noori
*Attorney, Agent, or Firm*—Wolf, Greenfield & Sacks, P.C.

[57] ABSTRACT

A technique for determining properties such as Young's modulus, coefficient of thermal expansion, and residual stress of individual layers within a multi-layered sample is presented. The technique involves preparation of a series of samples, each including one additional layer relative to the preceding sample. By comparison of each sample to a preceding sample, properties of the topmost layer can be determined, and residual stress at any depth in each sample, resulting from deposition of the top layer, can be determined.

40 Claims, 9 Drawing Sheets

OTHER PUBLICATIONS

T.W. Clyne et al., "The Effect of Intermediate Layers on Residual Stress Distributions and Debonding of Sprayed Thermal Barrier Coatings", in 3rd Int. Symp. on Structural and Functional Gradient Materials (FGM '94), B. Ilschner(ed), Lausanne, 1994.

J. Musil et al., "Plasma Spraying Deposition of Graded Thermal Barrier Coatings", Proceedings of the International Thermal Spray Conference & Exposition, Orlando, Florida, May 28–Jun. 5, 1992, pp. 525–530.

J. Musil et al., "Thermal Cycling, Oxidation Behavior and Mechanical Properties of Graded and Duplex PSZ TBC Coatings", 12th Int. Sym. on Plasma Chemistry, Aug. 21–25, 1995.

Alison L. Shull, Howard G. Zolla, and Frans Spaepen. "In Situ Study of Stresses in Ag/Cu Thin Film Multi–Layers During Deposition", Materials Research Society Fall Mtg., (1994), pp. 1–6.

J. Madeiski, "Solidification of Droplets on a Cold Surface", (Oct. 1975), pp. 1–6.

Mauro Ferrari, John R. Harding and Maurizio Marchese, "Simulation of Thermal Barrier Plasma–Sprayed Coatings", Mat. Res. Soc. Symp. Proc. vol. 190 (1991 Materials Research Society), 1–2.

S. J. Yankee and B. J. Pletka, "Effect of Plasma Spray Processing Variations on Particle Melting and Splat Spreading of Hydroxylapatite and Alumina", Journal of Thermal Spray Tech. vol. 2(3), Sep. 1993, pp. 271–281.

V.E. Belaschchenko and YU.B. Chernyak, "Stochastic Approach to the Modeling and Optimization of Thermal Spray Coating Formation", Journal of Thermal Spray Tech., vol. 2(2) Jun. 1993, pp. 159–164.

Reinhold Publishing Corporation, "Residual Stresses", (1954), pp. 271–283.

William R. Osgood, "Residual Stress in Metals and Metal Construction", (Reinhold Publishing Limited, New York 1954) pp. 271–283.

B. Borgerding, H.J. Sölter, E. Lugscheider, K. Simhan, "Modelling of Temperature Gradient and Stress–Strain Distributions during the Plasma Spraying Processs", pmi vol. 24 (1992), pp. 1–23.

Gerardo Trapaga and Julian Szekely, "Mathematical Modeling of the Isothermal Impingement of Liquid Droplets in Spraying Processes", (Metallurgical Transactions B), vol. 22B, Dec. 1991, pp. 901–914.

R. Knight and R.W. Smith, "Residual Stress in Thermally Sprayed Coatings", (Proceedings of the '93 Nat. Thermal Spray Conf., (Jun. 1993), pp. 1–35.

Keiro Tokaii, Takeshi Ogawa and Hideaki Shibata, "The effect of gas nitriding on fatigue behavior in pure titanium", (Butterworth–Heinemann Ltd.) Fatigue, 1994, vol. 16 Jul., pp. 331–336.

R. Knight and R.W. Smith, "Residual Stress in Thermally Spray Coatings", (Proceedings of the '93 Nat. Thermal Spray Conf. (Jun. 1993), pp. 607–612.

Kazumi Tani, Hiroshi Nakahira, Kiyoshi Miyajima and Yoshino Harada, "Thermal and Elastic Anisotropy of Thermally Sprayed Coatings", (Materials Transactions, JIM, vol. 33 No. 6 (1992) pp. 618–626.

METHOD AND APPARATUS FOR THE EVALUATION OF A DEPTH PROFILE OF THERMO-MECHANICAL PROPERTIES OF LAYERED AND GRADED MATERIALS AND COATINGS

This invention was made with government support under Contract No. DE-AC07-941D13223 awarded by the U.S. Department of Energy and Grant No. N00014-94-1-0139 awarded by the Department of the Navy. The government has certain rights in the invention.

FIELD OF THE INVENTION

The invention relates generally to surface deposition, and ore particularly to evaluation of the depth profile of thermo-mechanical properties of a layer of material deposited on a substrate using mechanical loading, thermal loading, and a combination.

BACKGROUND OF THE INVENTION

Layered materials, such as ceramic thermal-barrier coatings and wear-resistant coatings, are used in a broad range of engineering applications such as in high-temperature components of aircraft engines, and surfaces subjected to rolling and fretting contact wear and fatigue. Functionally-graded materials (FGMs) (within which the composition and microstructure, and hence the physical and mechanical properties, change gradually as a function of thickness, that is, along at least one axis) are increasingly being examined for a variety of coating and structural applications.

There are many known methods of fabricating surface coatings and layered structures of fixed or graded compositions. These include thermal spray, physical vapor deposition, chemical vapor deposition, e-beam evaporation, three-dimensional printing, powder metallurgy, and self-propagating high-temperature combustion synthesis. Irrespective of which of these methods is used for processing, there exist residual stresses in the layered structure upon cooling to room temperature from the processing temperature, due to, for example, thermo-mechanical incompatibility between phases, or non-uniform sintering of layered material. Indeed, deposition of any material on a substrate, whether it be layered, an FGM, or designed to be homogeneous, results in intrinsic stress in the deposited layer as a function of thickness. Such stresses build for a variety of reasons. In plasma-spray deposition, a melted material is sprayed onto a relatively cold substrate and, as it cools and solidifies on the substrate, it contracts, leading to an overall tensile force within the deposited layer in a direction parallel to the substrate surface. Other intrinsic stresses can result from crystallization and other intermolecular rearrangements that occur upon solidification and that result in a volume change in the deposited material upon solidification. These intrinsic stresses typically result in deformation of the substrate to some extent, and can lead to decohesion, internal cracking, and other mechanical failure.

Additionally, in layered materials properties such as Young's modulus and the coefficient of thermal expansion may vary as a function of thickness.

A knowledge of the magnitude and spatial distribution of internal stresses is essential to developing a proper understanding of the mechanical response of the structure and to optimizing its performance. In addition, the physical and mechanical properties (such as Young's modulus and the coefficient of thermal expansion) of the deposited layer itself are strongly influenced by the processing condition, and cannot be easily estimated using conventional techniques known for bulk samples.

Significant effort has been made to determine, both theoretically and experimentally, intrinsic stresses in deposited materials, but techniques for assessing such properties can lack accuracy and spatial resolution, and can be inflexible and not cost effective. Some of these efforts have involved In situ testing of characteristics of a deposited material and/or substrate during deposition. For example, during a thermal spray deposition, a change in curvature of the substrate during deposition has been measured by visual observation or video record, or traveling microscope (see, for example, Gill et al. "Monitoring of Residual Stress Generation During Thermal or Plasma Spraying by Curvature Measurements", Proceedings of the Seventh National Thermal Spray Conference, Jun. 20–24, 1994, Boston, Mass.; Howard, et al. "The Effect of Residual Stresses on the Debonding of Coatings Under an Applied Load", Proceedings of the Seventh National Thermal Spray Conference, Jun. 20–24, 1994, Boston, Massachusetts; Clyne, et al. "The Effect of Intermediate Layers on Residual Stress Distributions and Debonding of Sprayed Thermal Barrier Coatings", third International Symposium on Structural and Functional Gradient Materials (FGM '94), B. Ilschner (ed.) PPUR Lausanne 1994; Gill, et al. "Stress Distributions and Material Response in Thermal Spraying of Metallic and Ceramic Deposits", *Metallurgical Transactions B* 21B, 377 (April, 1990)).

Shull, et al., "In situ Study of Stresses in Ag/Cu Thin Film Multilayers During Deposition", Materials Research Society Fall Meeting 1994, Boston, Mass., describe deposition of Ag/Cu multilayers onto a thin silicon substrate. During deposition, the force per unit width in the multilayers is calculated from the substrate curvature, which is continuously measured by a laser scanning technique.

One drawback of In situ measurements is that visual observation and video recordation can be quite inaccurate. Another drawback is that, because solidification and intermolecular rearrangement may occur during processing which causes redistribution of stresses, and may cause a change in properties, and therefore may not be complete at any given depth until significant material has been deposited, data as a function of depth can be inaccurate.

Tani, et al., in "X-ray Stress Measurement of Thermal Sprayed Coatings at Elevated Temperatures", *Advances in Thermal Spraying,* Tani, et al., Welding Institute of Canada, Pergaman Press, 1986, Proceedings of the 11th International Thermal Spray Conference, page 605, use X-ray stress measurements to characterize stresses resulting from thermal-spray techniques. Various materials, at various thicknesses, are deposited and subjected to X-ray analysis to determine stress.

Hardness of material as a function of depth has been estimated by probing a cross section of a deposited layer. (Tokaji, et al., "The Effect of Gas Nitrating on Fatigue Behavior in Pure Titanium", *Fatigue,* 16, 331 (July 1994)). However, analysis of a cross section can be inaccurate since partitioning a layer to obtain a cross section for analysis relieves a significant amount of intrinsic stress near the surface to be tested. That is, a cross section of material often is not representative of a depth profile of the material since properties of the material can be changed and additional residual surface stresses can be induced by the act of cutting the material to expose the cross section. Additionally, many materials are orthotropic (in-plane properties differ from out-of-plane properties), thus hardness testing (which combines information on both in-plane and out-of-plane properties) will not give accurate values of in-plane properties.

Another technique for investigating the depth profile of stress in a material involves depositing a layer of material and then removing very thin layers of the deposited material and performing curvature testing after each removal step. (e.g., Greving, et al., "Residual Stress Evaluations of Thermal Spray Coatings by a Modified Layer Removal Method", Proceedings of the Seventh National Thermal Spray Conference, Jun. 20–24, 1994, Boston, Mass.). However, the removal process itself can change the stress state at the depth at which the layer is removed, leading to inaccuracy, and the technique is relatively labor-intensive.

Another technique for determining stress as a function of depth involves drilling one or more holes in a deposited layer, attempting to determine a change in strain about the hole, and thereby estimating a change in stress due to a combination of original stress and stress due to the hole drilling (Bialucki, et al., "Residual Stresses Measurement of Plasma Sprayed Coatings" *Advances in Thermal Spraying*, page 837, Bialucki, et al., Welding Institute of Canada, Pergaman Press, 1986, Proceedings of the 11th International Thermal Spray Conference). However, hole drilling changes the stress state in a way that is quite complex and like the layer-removal process. That is, each of the layer-removal process and the hole-drilling process seeks to measure stress within the material without the removed material present, but the process of material removal itself can cause changes within the remaining material due to the abrasive nature of the removal process.

Chiu, in an article entitled "Residual Stresses in Ceramic Coatings as Determined from the Curvature of a Coated Strip", *Materials Science and Engineering*, A150, 139–148 (1992) describes a technique involving depositing a single layer of material on a substrate, applying load to the substrate and determining a deflection value associated with the applied load, and estimating residual stress in the coating. Only a single layer of material on a substrate is investigated.

Accordingly, it is an object of the present invention to evaluate, reliably, systematically, conveniently, and inexpensively, the thermo-mechanical properties as a function of depth in a layer of material, in multi-layered materials, and/or in functionally graded materials, specifically the in-plane Young's modulus, the in-plane coefficient of thermal expansion, and the in-plane residual stresses arising from processing.

SUMMARY OF THE INVENTION

The present invention provides a technique for evaluating thermo-mechanical properties, as a function of depth, in a layer of material and in multi-layered materials. The technique involves providing a series of samples, each of which is identical to a preceding sample with the exception that an additional layer of material is provided. That is, rather than providing a product, removing a layer, and measuring properties, removing another layer and measuring properties, etc., the invention provides samples representative of stopping points in a deposition process and which can be tested and compared to determine several properties.

According to one aspect the invention provides a method which involves providing a first sample including a first film, and sample that is multi-layered, the second sample including the first film and a second film on the first film. Values of thickness, Poisson ratio, and average coefficient of thermal expansion of the first sample are provided, along with values of stiffness, neutral axis position, and average Young's modulus of the second sample and a value of Young's modulus of the second film. A curvature value of each of the first and second samples at at least two different temperatures is measured to obtain a value of curvature variation between the first and second samples as a function of temperature, and then coefficient of thermal expansion of the second film is determined.

According to another aspect the invention provides a method of determining residual stress. The method involves providing first and second samples as described above, and providing values of thickness and Poisson ratio of the first sample, and stiffness, neutral axis position, and average Young's modulus of the second sample and Young's modulus of the second film. A curvature variation value of the second sample relative to the first sample is measured while a uniform temperature distribution value exists in the second sample. Residual stress of the second film is thereby determined.

According to another aspect the invention provides a method of determining Young's modulus of a film of a multi-layered sample. The method involves providing a first multi-layered sample including at least a first film and a second film on the first film, and a second multi-layered sample including at least the first film, the second film on the first film, and a third film on the second film. Values of stiffness, neutral axis position, and average Young's modulus of the first sample are provided, along with thickness of the third film. The stiffness of the second sample then is measured and Young's modulus of the third film is determined.

According to another aspect the invention provides apparatus that can be used to apply a load to a sample and measure resulting curvature of the sample optically. The apparatus includes a stage for mounting a film, an emitter of electromagnetic radiation positioned to direct electromagnetic radiation at a surface of the film, and a load source positioned to apply a load to a surface of the film. The load source can be constructed to apply a bending force to the film, and can be a four-point bending apparatus. The apparatus also can include a source of thermal energy for heating the film.

According to another aspect the invention provides a method for applying a bending force to a sample while determining curvature resulting from the applied bending force optically. The method involves providing a sample, applying a bending force to the sample, and simultaneously directing electromagnetic radiation at a surface of the sample and measuring an angle of deflection of the electromagnetic radiation from the surface, thereby determining curvature of the sample due to the applied bending force. The bending force can be applied using a four-point bending apparatus. The method also can involve analysis of a variety of multi-layered samples and determination of Young's modulus, residual stress, and coefficient of thermal expansion at various layers within a sample.

Other advantages, novel features and objects of the invention will become apparent from the following detailed description of the invention when considered in conjunction with the accompanying drawings.

DETAILED DESCRIPTION OF THE INVENTION

The present invention provides a technique for determining properties such as Young's modulus (E), residual stress (σ), and coefficient of thermal expansion (α) of a multi-layered sample.

Figure 1:
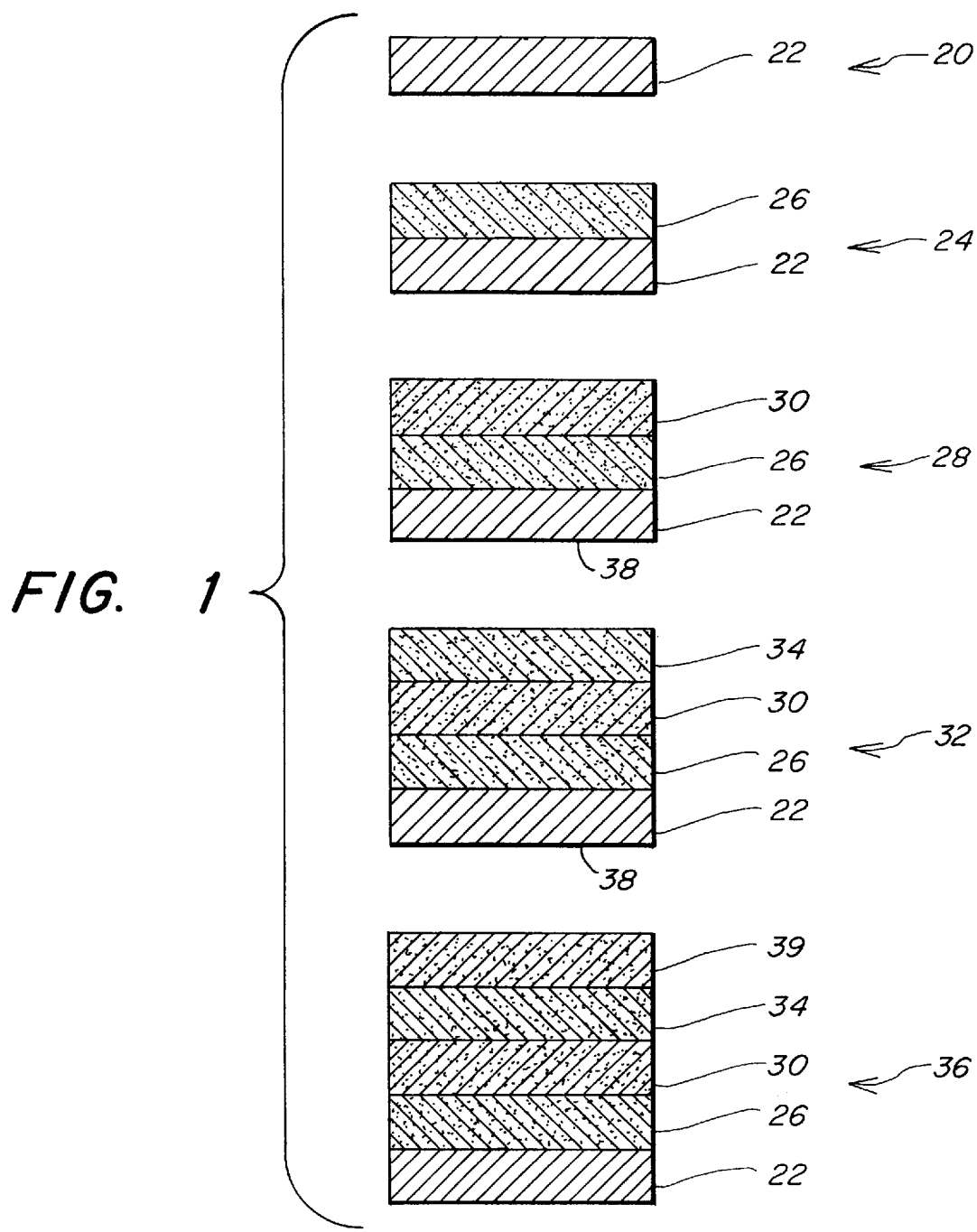
FIG. 1 illustrates schematically a plurality of samples, one of which is a bare substrate and the rest of which each include a substrate and one or more films deposited on the substrate.

Referring to FIG. 1, a plurality of individual samples are illustrated schematically that, when subjected to certain experiments, will provide a profile as a function of depth of a final, multi-layered product. FIG. 1 is not drawn to scale. In all of the figures, like components are represented by like numerals.

A sample 20 includes a single film 22 of a first material. Typically, the first film 22 of material is a substrate such as a steel substrate. A sample 24 is a bi-layer structure including a first film 22 identical to the first film 22 of sample 20, and a second film 26 on the first film. As illustrated, the first film 22 is a steel substrate and the second film 26 is layer of a different material, for example a layer of a metal such as nickel, a ceramic, or a metal/ceramic composite deposited on the substrate. A three-layer sample 28 includes steel substrate 22, second film 26 identical to layer 26 of sample 24 and a third film 30 composed of a material the same as or different from the material of layer 26 deposited on the second film 26. A four-layer sample 32 includes substrate 22, second film 26, and third film 30 identical to the three layers of sample 28, and an additional, fourth film 34 on film 30. Sample 36 is identical to sample 32 but includes a fifth film 39 on film 34. Thus, samples 20, 24, 28, 32, and 36 represent stopping points during the creation of multi-layered sample 36 by, for example, plasma spray, chemical vapor deposition, physical vapor deposition, and the like, where the various layers can be the same material or different material. The samples are created by carrying out a deposition process that, if taken to completion, would result in the five-layer sample 36, by stopping the process at successively increasing layering steps.

The procedure used to create samples of the invention such as samples 20–36 is to be distinguished from a procedure that would involve preparing a five-layered sample 36, performing experiments on that sample, removing the top layer 39 to create a sample similar to sample 32 and performing experiments, then removing the next layer 34 to create a sample similar to sample 28 and performing experiments, etc. The latter technique can alter stress states within the sample due to the process of removing material itself. That is, each sample of the invention includes a top film having a first side adjacent the next-to-top film and a second, opposing, upwardly-facing film having not had additional material applied thereto, that is, each sample represents the termination of the deposition process rather than a surface exposed by removal of a deposited layer.

The five samples 20, 24, 28, 32, and 36 are to be understood as representative of any combination of at least two samples in which each sample containing n−1 layers is essentially identical to the sample containing n layers with the exception that the topmost layer is not present in the n−1 sample. The samples illustrated are taken to be representative of any number of layered samples that satisfy this criterion.

Experimentation involving the samples illustrated in FIG. 1 will be described with reference to samples 28 and 32. In a typical procedure, essentially identical substrates 22 are fabricated for each of samples 28 and 32. Each of substrates 22 includes a reflective surface 38 that can be illuminated with a laser beam to measure curvature as will be described below. Since surfaces 38 of substrates 22 in samples 28 and 32 will not be absolutely identical, curvature at room temperature of each of substrates 22 for samples 28 and 32, respectively, are measured prior to any deposition to establish a baseline curvature for each. Then, for sample 28, layers 26 and 30 are deposited. For sample 32, layers 26, 30 and 34 are deposited. After the deposition process is complete for each sample, the curvature of each sample is measured via laser reflectance from surface 38 of each substrate. For each sample, a difference in curvature prior to deposition and subsequent to deposition is thereby defined. It is to be understood that any means of determination of curvature can be employed, for example application of a strain gauge to surface 38 of substrate 22 which will indicate curvature of the substrate resulting from the deposition process. Determination of a curvature variation value (prior to and subsequent to deposition) of sample 32 relative to sample 28 will be useful, as described more fully below.

In a second test, each of samples 28 and 32, after deposition, are subjected to a bending force and curvature of each sample is measured as a function of the applied bending force. In another experiment, curvature of each of samples 28 and 32 is measured at, at least, two different temperatures, and a curvature variation value between the two samples as a function of temperature is established. The latter experiment typically is conducted by scanning temperature and simultaneously measuring curvature. It can be desirable to limit bending and temperature to the extent that no plasticity is induced in the specimen or sample, since additional residual stresses will be induced and the inventive analysis can thereby be complicated.

Figure 2:
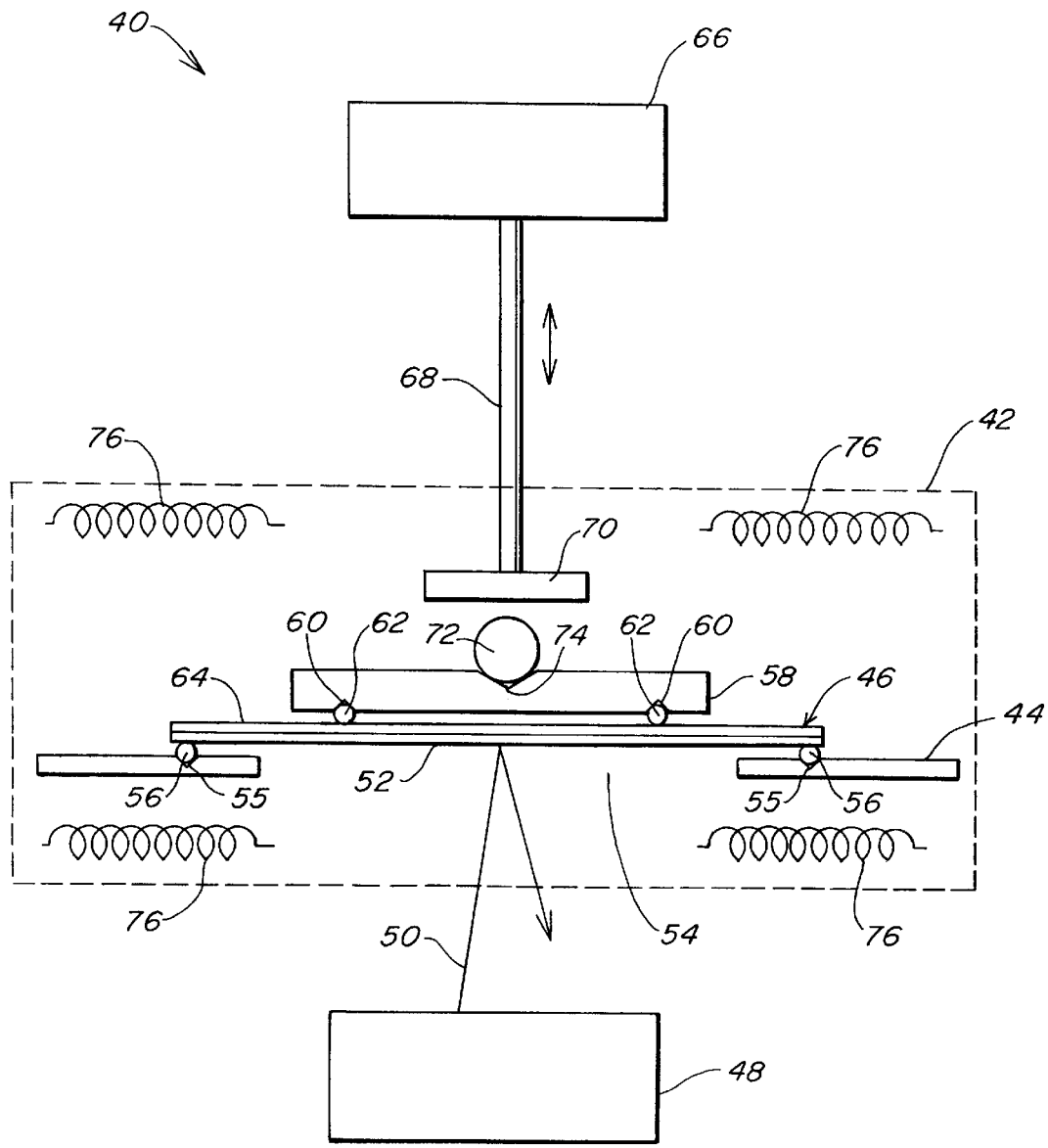
FIG. 2 illustrates schematically apparatus of the invention that is a combination of a four-point bending apparatus and a laser-scanning curvature measurement device.

Referring now to FIG. 2, apparatus 40 according to one aspect of the invention for measuring curvature of a film or layered sample during application of a load is illustrated schematically. The illustration, in part, is representative of a commercially-available arrangement for measuring change in radius of curvature of a substrate caused by deposition of a stressed thin film, such as that available from Tencor, Inc. of Mountain View, Calif., under the designation FLX-2900. The commercially-available arrangement FLX-2900 includes a laser for measuring a change in radius of curvature of a substrate caused by stress imparted to the substrate by, for example, a material deposition process. The commercially-available arrangement FLX-2900 does not, however, include an arrangement for applying a bending force to the substrate. This specific commercially-available machine is noted for illustrative purposes only. Any of a variety of similar machines would be suitable for use in accordance with the invention.

Apparatus 40 includes an enclosure 42 within which is a stage 44 positioned to mount a sample 46 (a bi-layer sample is illustrated). A source 48 of a laser beam 50 is positioned to direct a laser beam 50 at a reflective surface 52 of sample 46. Typically, surface 52 will be the side of a substrate opposite the side upon which layers of material are deposited. An opening 54 in stage 44 allows for passage of the laser beam through the stage and to surface 52 of the sample.

Apparatus 40 includes an arrangement for applying a standard four-point bend force to sample 46. Stage 44 includes indentations 55 within which reside contact members 56 projecting above the stage and upon which surface 52 of sample 46 rests. Above sample 46 is a member 58 including indentations 60 within which reside contact members 62 that project downwardly toward sample 46 to an extent greater than does any surface of member 58. Stage 44, member 58, and contact members 56 and 62 can be constructed of any suitable material, for example steel. Contact members 56 contact bottom surface 52 of sample 46 near the lateral border of the sample, and contact members 62 contact a top surface 64 of sample 46 centrally relative to the position of contact members 56. Thus, when a force is applied to member 58 in a direction of sample 46, sample 46 will be bent. A load source 66 applies a load, via a shaft 68, to a load member 70 that impinges upon a contact member 72 residing within an indentation 74 of member 58.

A four-point bending apparatus is illustrated as preferred. The apparatus of this aspect of the invention involves any arrangement for applying a bending force to a film and measuring curvature of the film resulting from the applied bending force. Laser scanning apparatus to measure curvature, in combination with a four-point bending apparatus, is presented as one aspect of the invention.

Enclosure 42 of the apparatus 40 includes a source of thermal energy, represented by a series of coils 76. Any thermal source, such as a source of electromagnetic radiation, can be used. During some experimental procedures useful in the invention, no thermal energy is needed.

Methodology will now be described. For purposes of clarity, the following definitions of symbols used in equations and figures is given:

properties of the topmost layer of a sample:

| | |
|---|---|
| $\Delta h$ | Thickness |
| $E_h$ | Young's modulus |
| $\upsilon$ | Poisson's ratio of the layer assumed |

-continued

| | |
|---|---|
| | constant through the thickness |
| $\alpha_h$ | Coefficient of thermal expansion |
| $\sigma^T_h$ | Residual stresses at temperature T | global properties of a sample:

| | |
|---|---|
| h | Thickness |
| $\bar{E}$ | Average Young's modulus |
| $z_N$ | Position of the neutral axis |
| I | Stiffness |
| $\bar{\alpha}$ | Average coefficient of thermal expansion |
| $\Delta k$ | Curvature variation before and after deposition |
| dk/dT | Curvature variation with temperature |

Subscript 0 refers to a property of a "first sample", such as sample 28.

Subscript 1 refers to properties of a "second sample", for example sample 32.

Figure 3:
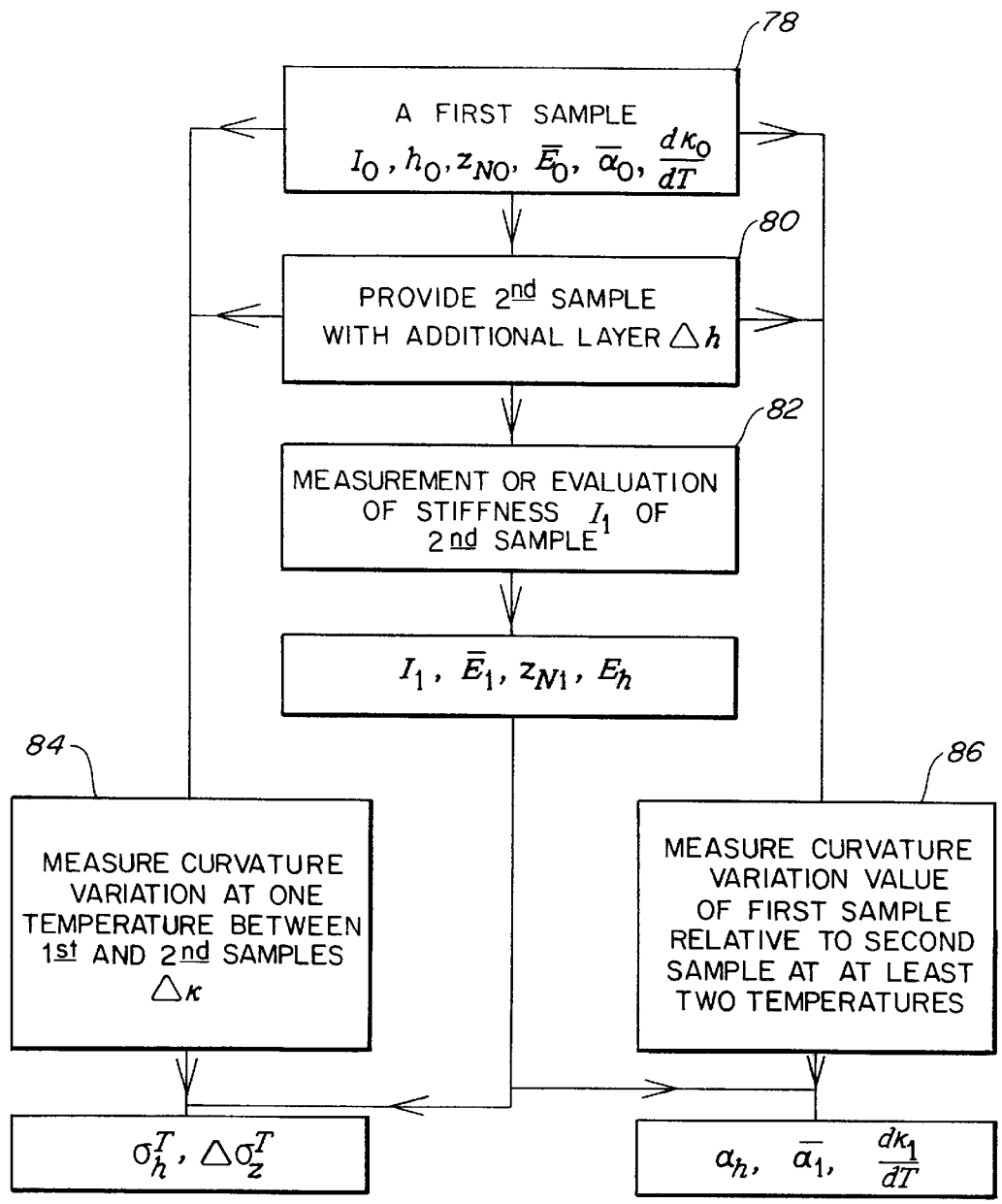
FIG. 3 is a flow chart illustrating methodology for determining Young's modulus, intrinsic stress, and coefficient of thermal expansion as a function of depth of a multi-layered sample.

Referring now to FIG. 3, a flow chart outlining an experimental procedure in accordance with the invention is illustrated. In step 78, a first sample (such as a three-layer sample 28) and properties including stiffness of the first sample ($I_0$), thickness ($h_0$), neutral axis position ($z_{N0}$), and average Young's modulus of the first sample ($\bar{E}_0$) are provided. Step 80 represents provision of a second sample with an additional layer, such as sample 32 including additional layer 34 relative to sample 28. The difference in thickness ($\Delta h$) due to addition of the additional layer is provided, such as by measurement. Step 82 represents application of a bending force to the second sample and the measurement of curvature of the second sample resulting from application of the bending force (using, for example, apparatus 40 illustrated in FIG. 2). This experiment provides, as described more fully below, Young's modulus of the added layer ($E_h$), average Young's modulus of the second sample ($\bar{E}_1$), and neutral axis position of the second sample ($z_{N1}$). Thus, with reference to FIG. 1, subjecting any two samples 20 and 24, 24 and 28, 28 and 32, or 32 and 36 to a bending force while measuring curvature of the sample resulting from application of the bending force will give Young's modulus of the top layer of the sample having the most layers. If, for example, samples 24 and 28 are compared and Young's modulus of top layer 30 is established, then in five-layer sample 36 Young's modulus at layer 30 is known.

A further experiment, represented at 84 of FIG. 3 involves measurement of curvature variation value of the first and second samples at one temperature, for example room temperature. As discussed, a curvature value of each substrate is measured prior to deposition, then a curvature value of each sample is measured after deposition is complete, providing a curvature variation value for each of the first and second samples due to deposition. Then, a curvature variation value of the first sample relative to the second sample can be established and this, along with properties determined in the bend test at 82, provide values of residual stress ($\sigma^T_h$) in the top layer of the second sample, and can be used to derive residual stress in any layer of a multi-layered sample, for example layer 30 in sample 36, resulting from the deposition process. With reference to sample 36 of FIG. 1, residual stress at layer 30 will be one value when layer 30 is the top layer (as in sample 28), a second value when a single subsequent layer is added (sample 32), and will be yet a different value when two additional layers are added (sample 36). The variation in residual stress ($\Delta\sigma^T_z$) of any layer at position z due to addition of the new layer of the multi-layered structure can be determined in accordance with the invention.

Another experiment, represented at 86 in FIG. 3, involves measurement of a curvature variation value between a first and a second sample while scanning temperature, or at at least two different temperatures for each sample. The results of this experiment, along with data from experiment 82 involving measurement of curvature during bending, provides values of coefficient of thermal expansion of the top layer of the second sample ($\alpha_h$), and average coefficient of thermal expansion of the entire second sample ($\overline{\alpha_1}$).

Figure 4:
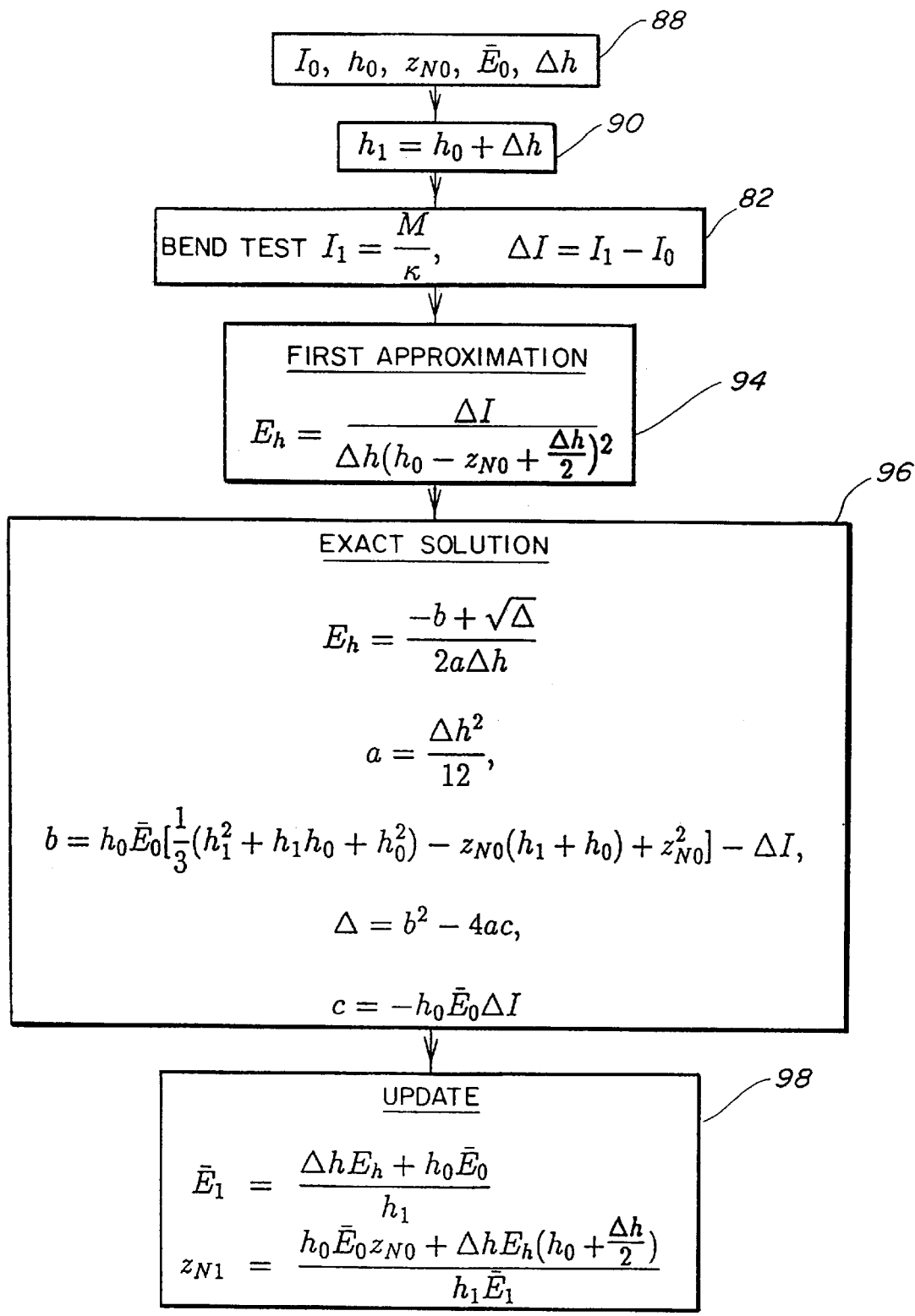
FIG. 4 is a flow chart illustrating methodology for determining Young's modulus.

Referring now to FIG. 4, a flow chart illustrates derivation of Young's modulus of a layer of a multi-layered sample (steps 78, 80, 82 of FIG. 3) in detail. At 88, $I_0$, $h_0$, $z_{N0}$, and $\overline{E}_0$ for a first sample (e.g., sample 28) are provided, along with $\Delta h$ representing the thickness of the top layer of a second sample that is identical to the first sample but including an additional layer (e.g., sample 32). Thickness of the entire second sample ($h_1$) is computed at 90. Subjection of the second sample to a bend test at step 82 provides a value of stiffness of the second sample ($I_1$) and a value of difference in stiffness between the first and second samples ($\Delta I$). At 94, a first approximation of Young's modulus of the top layer of the second sample ($E_h$) is provided (see Equation 5, below). In step 96, an exact solution of $E_h$ is provided (see Equations 5–10, below). In step 98, average Young's modulus of the second sample ($\overline{E}_1$) and neutral axis position of the second sample ($z_{N1}$) also are provided (see Equations 11 and 12, below). With reference again to FIG. 1 and sample 28 as the first sample and sample 32 as the second sample, it can be seen that the data provided in step 98 (Young's modulus and neutral axis position of the second sample 32) will be useful when sample 32 is compared with sample 36, with sample 32 as the first sample and sample 36 as the second sample (see information required at step 88). Information required in step 88 is originally provided by starting with a substrate 22 (sample 20) in which all required values are known or easily determined. Investigation of each sample results in information as to that sample, the top layer of that sample, and this information then can be used to derive information for each succeeding sample and for determination of residual stress and coefficient of thermal expansion, described below.

Figure 5:
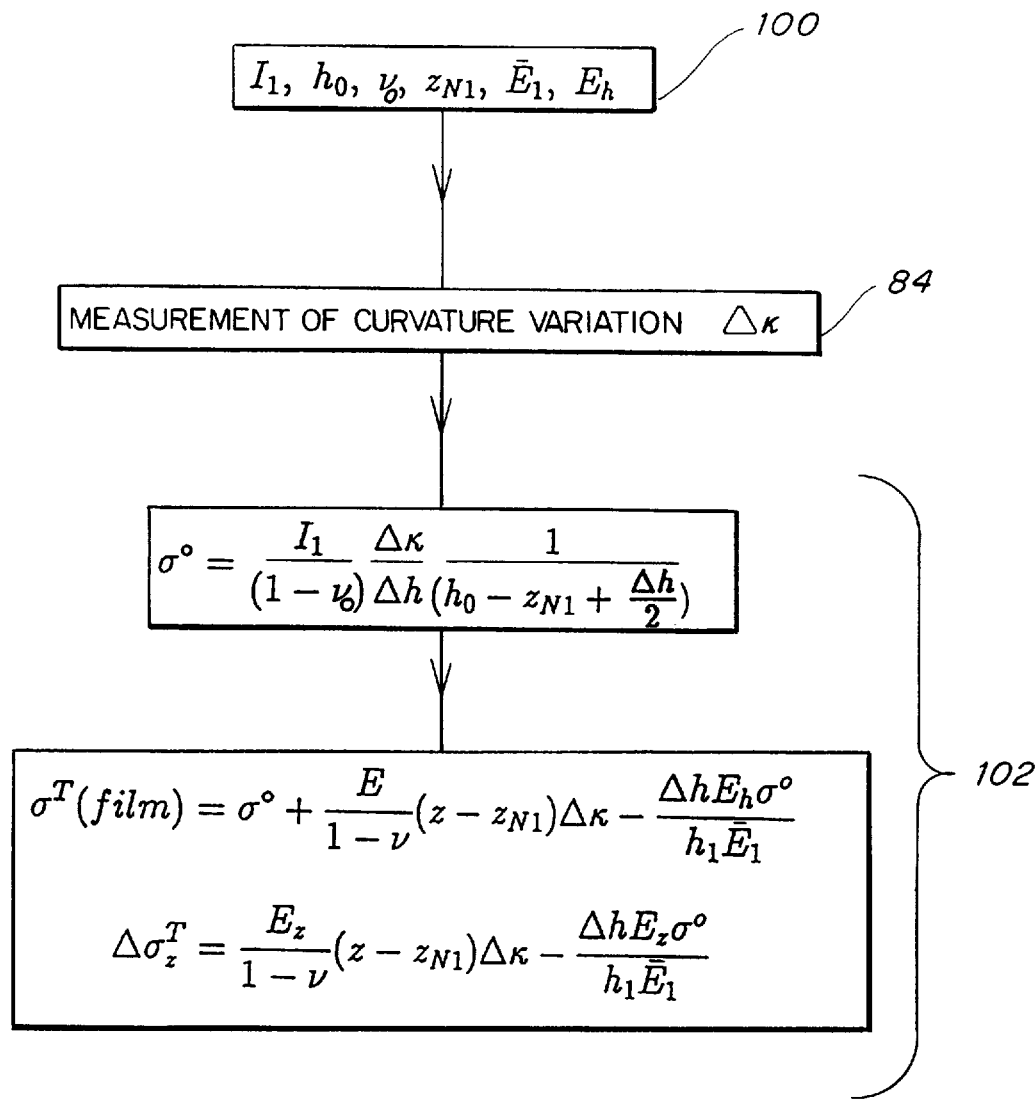
FIG. 5 is a flow chart illustrating methodology for determining residual stress.

Referring now to FIG. 5, a flow chart illustrating determination of residual stress (see step 84 of FIG. 3) is provided, with added detail. Reference will be made to a first sample 28 and a second sample 32 (FIG. 1), as above. At step 100, stiffness of the second sample ($I_1$), thickness of the first sample ($h_0$), Poisson ratio of the top layer (v), neutral axis position of the second sample ($z_{N1}$), average Young's modulus of the second sample ($\overline{E}_1$), and Young's modulus ($E_z$) of an underlying layer, the residual stress of which is to be determined, are provided. These values can be provided from experimentation used to derive Young's modulus (FIG. 4) or, where coating thickness is much smaller than substrate thickness, for a small variation in thickness the variation of curvature of a sample can provide values of intrinsic stress in the added layer. Then, a curvature variation value of the first sample relative to the second sample at one temperature is measured at step 84. At step 102, residual stress ($\sigma^T_h$) and variation in the stress of any layer at any position through the thickness of the sample ($\Delta \sigma^T_z$) can be determined (see Equations 19–21, below).

Figure 6:
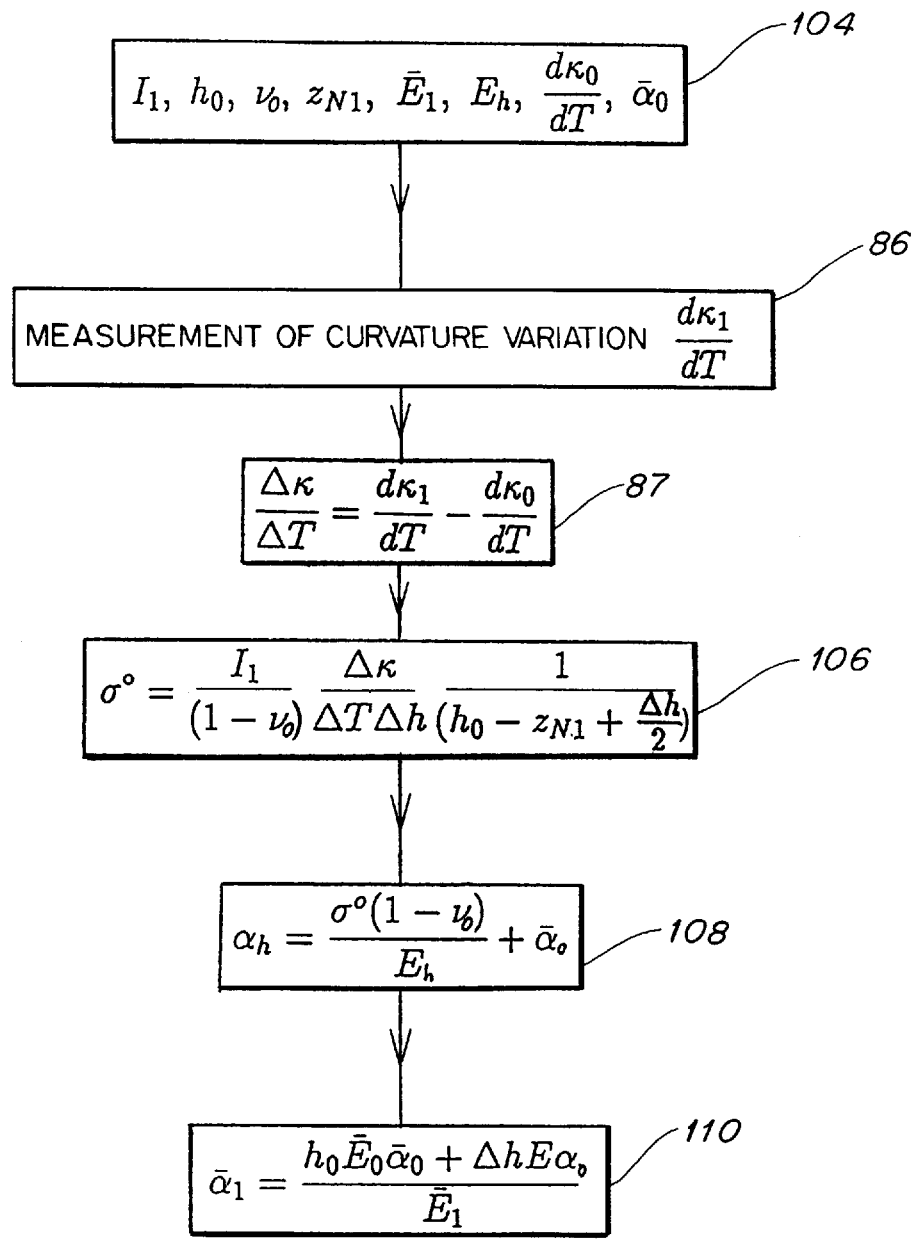
FIG. 6 is a flow chart illustrating methodology for determining coefficient of thermal expansion.

Referring now to FIG. 6, determination of coefficient of thermal expansion (step 86 of FIG. 3) is described in greater detail. At step 104, the parameters $I_1$, $h_0$, v, $z_{N1}$, $\overline{E}_1$, $E_z$, described above, are provided along with values of curvature variation, value of the first sample as a function of temperature, and average coefficient of thermal expansion of the first sample ($\overline{\alpha_1}$). Step 86 (see also FIG. 3) involves measurement of the curvature variation of the second sample as a function of temperature using, for example, a standard Tencor FLX-2900 machine, and calculation of the curvature variation value of the first sample relative to the second sample ($\Delta k$). Step 106 involves Equation 17, below. At step 108, coefficient of thermal expansion ($\alpha_h$) of the added layer is calculated (see Equation 16, below) and at step 110, average coefficient of thermal expansion of the second sample is determined (see Equation 18, below).

Mathematical and theoretical methodology is now presented in greater detail.

Determination of Young's Modulus

We consider a multilayered plate or beam for which we know initially the total thickness, $h_0$, the average Young's modulus $\overline{E}_0$ and the position of the neutral axis, $z_{N0}$ and the beam stiffness, $I_0$. These characteristics can be computed from the material distribution though the thickness.

$$\overline{E}_0 = \frac{1}{h_0} \int_0^{h_0} E(z) dz \tag{1}$$

$$z_{N0} = \frac{1}{\overline{E}_0} \int_0^{h_0} zE(z) dz \tag{2}$$

$$I_0 = \int_0^{h_0} z^2 E(z) dz - (z_{N0})^2 h_0 \overline{E}_0 \tag{3}$$

For the trivial case of an homogeneous substrate, $\overline{E}_0$ is the Young's modulus of the substrate, $E_s$, $z_{N0}$ is equal to $h_0/2$ and the beam stiffness, $I_0$, is equal to $E_s h^3_0/12$.

After deposition of the new layer of thickness $\Delta h$ for which we want to determine the Young's modulus, the total thickness of the beam is $h_1 = h_0 + \Delta h$.

Experimental measurement: stiffness of the beam $I_1$

The stiffness of the beam can be measured experimentally by evaluating the curvature, $\kappa$, of the beam loaded with a constant moment, M. The stiffness $I_1$ is then equal to $$I_1 = M/\kappa \tag{1}$$

From the variation of the stiffness, $\Delta I = I_1 - I_0$, it is possible to deduce the Young's modulus of the added layer. A first approximation of the Young's modulus when $\Delta h$ is much smaller than $h_0$ is $$E_h = \frac{\Delta I}{\Delta h \left( h_0 - z_{N0} + \frac{\Delta h}{2} \right)^2}.$$

The exact solution is given by $$E_h = \frac{-b + \sqrt{\Delta}}{2a\Delta h}$$

where $$a = \frac{\Delta h^2}{12}, \tag{7}$$

-continued $$b = h_0 \overline{E}_0 \left[ \frac{1}{3} (h_1^2 + h_1 h_0 + h_0^2) - z_{N0}(h_1 + h_0) + z_{N0}^2 \right] - \Delta I, \quad (8)$$

$$\Delta = b^2 - 4ac, \quad (9)$$

$$c = -h_0 \overline{E}_0 \Delta I \quad (10)$$

Once the Young's modulus of the added layer has been evaluated, the general characteristics of the beam can be updated as follow $$\overline{E}_1 = \frac{\Delta h E_h + h_0 \overline{E}_0}{h_1} \quad (11)$$

$$z_{N1} = \frac{h_0 \overline{E}_0 z_{N0} + \Delta h E_h \left( h_0 + \frac{\Delta h}{2} \right)}{h_1 \overline{E}_1} \quad (12)$$

Determination of the Coefficient of Thermal Expansion

What we need to know about the beam: $I_1$, $h_0$, $\nu$, $z_{N1}$, $\overline{E}_1$, $E_h$, $\overline{\alpha}_0$ and $d\kappa_0/dT$ where $$\overline{\alpha}_0 = \frac{1}{h_0 \overline{E}_0} \int_0^{h_0} E(z) \alpha(z) dz \quad (13)$$

$$\frac{d\kappa_0}{dT} = \frac{1}{I_0} \int_0^{h_0} (z - z_{N0}) E(z) \alpha(z) dz. \quad (14)$$

For the trivial case of a homogeneous substrate, $\overline{\alpha}_0$ is equal to the coefficient of thermal expansion of the substrate, $\alpha_s$, and $d\kappa_0/dT$ is equal to zero.

Experimental measurement: curvature variation with temperature.

The unique measurement we have to consider is the curvature response of the plate under a small thermal excursion. This provides the parameter, $d\kappa_1/dT$ of the new plate. We define the curvature variation, $\Delta \kappa$, per change in temperature $\Delta T$, as $$\frac{\Delta \kappa}{\Delta T} = \frac{d\kappa_1}{dT} - \frac{d\kappa_0}{dT}. \quad (14)$$

The coefficient of thermal expansion of the added layer is then obtained by $$\alpha_h = \frac{\sigma^o (1 - \nu)}{E_h} + \overline{\alpha}_0 \quad (16)$$

where $$\sigma^o = \frac{I_1}{(1 - \nu)} \frac{\Delta \kappa}{\Delta T \Delta h} \frac{1}{\left( h_0 - z_{N1} + \frac{\Delta h}{2} \right)}. \quad (17)$$

The average thermal expansion of the new beam can be updated by $$\overline{\alpha}_1 = \frac{h_0 \overline{E}_0 \overline{\alpha}_0 + \Delta h E_h \alpha_h}{h_1 \overline{E}_1} \quad (18)$$

Determination of the Residual Stresses Due to Processing

The knowledge of $I_1$, $h_0$, $\Delta h$, $\nu$, $z_{N1}$, $\overline{E}_1$, $E_h$ is enough to compute the exact stress state in the new added layer. Here we assume that the non elastic strain resulting from processing in the added layer is uniform through the thickness of this new layer.

Experimental measurement: curvature variation before and after processing

The curvature of the wafer has to be evaluated before and after processing at a given temperature T. The variation of curvature, $\Delta \kappa$ is enough to provide internal stress distribution in the plate due to strain mismatch between substrate and the new added layer.

The stress in the added layer at the temperature T is equal to $$\sigma^T(z) = \sigma^o + \frac{E_h}{1 - \nu} (z - z_{N1}) \Delta \kappa - \frac{\Delta h E_h \sigma^o}{h_1 \overline{E}_1}, \quad (19)$$

where $$\sigma^o = \frac{I_1}{(1 - \nu)} \frac{\Delta \kappa}{\Delta h} \frac{1}{\left( h_0 - z_{N1} + \frac{\Delta h}{2} \right)}. \quad (20)$$

The strain mismatch in the added layer will also alter the stress state in the substrate. The variation of the stress in the substrate at the position through the thickness $\kappa$ due to the presence of the new added layer is equal to $$\Delta \sigma_z^T = \frac{E_z}{1 - \nu} (z - z_{N1}) \Delta \kappa - \frac{\Delta h E_z \sigma^o}{h_1 \overline{E}_1} \quad (21)$$

where $E_z$ is the Young's modulus at the position z.

Theory

Summary of equations to compute the stress and strain mismatch with the curvature history or the strain history for general multilayered materials.

Notations

The present analysis is considered for a multi-layered plate under internal axisymmetric loading due to strain mismatch during processing. No restriction is given to the material distribution through the thickness.

The growth of the material is characterized by an increasing thickness of the plate, h.

The position through the thickness is given by the height, z, from the back of the substrate. Let $E_{Bi}(z)$ be the biaxial Young's modulus given by $$E_{Bi}(z) = \frac{E(z)}{1 - \nu(z)} \quad (1)$$

where $E(z)$ and $\nu$ are the Young's modulus and the Poisson's ratio, respectively, at the height z. Similar analysis can be made of the case of a pure in-plane shear problem by changing $E_{Bi}$ with the shear modulus, $\mu(z)$.

We use the reduced stiffness coefficients of the plate, $A(h)$, $B(h)$ and $D(h)$, which are functions of the the thickness h, given by $$A(h) = \int_0^h E_{Bi}(z) dz, \quad (2)$$

$$B(h) = \int_0^h z E_{Bi}(z) dz, \quad (3)$$

-continued $$D(h) = \int_0^h z^2 E_{Bi}(z)dz. \quad (4)$$

The definition of B(h) and D(h) are not unique since they depend on the position of the plane z=0. Therefore, it is convenient to introduce the neutral axis height, $z_N$, and the axisymmetric "bending" modulus of the plate, $I_E$ given by $$z_N(h) = \frac{B}{A} \text{ and } I_E = D - z_N^2 A = \frac{DA - B^2}{A}. \quad (5)$$

During the analysis, a characteristic position, A, is also introduced equal to $$\lambda(h) = \frac{I_E}{A(h - z_N)}. \quad (6)$$

Experimental Evaluation of A, B and D

A four-point bend test can provide enough information to deduce the three parameters A, B and D in the case of a deposited coating on a substrate. It is important to note that a four point bend test will provide the stiffness under unidirectional moment and not under biaxial moment. As a first approximation, we consider that the Poisson's ratio does not vary through the thickness. This implies that all the parameters differ by a factor of (1–ν) where ν is the Poisson's ratio.

Let us consider the initial substrate for which A, B and D are supposed to be known. For a homogeneous substrate, for example, the three parameters are given by A=hE, B=Eh²/2 and D=Eh³/3. Then, $z_N$=h/2 and I=Eh³/12.

If we consider the deposition of a small layer of new material of thickness, δh, the variation of the three parameters is given by $$\delta A = E(h)\delta h, \ \delta B = hE(h)\delta h \text{ and } \delta D = h^2 E(h)\delta h \quad (7)$$

where E(h) is the Young's modulus of the deposited layer.
The variation of the position of the neutral axis is equal to $$\partial z_N = \frac{E(h)(h - z_N)}{A} \partial h \quad (8)$$

$$\partial I = (h - z_N)^2 E(h) \partial h \quad (9)$$

Experimentally, it is possible to detect the variation of the bending stiffness, I, by conducting a four point bend test. The evaluation of the variation of I is enough to provide the Young's modulus E(h).

$$E(h) = \frac{1}{(h - z_N)^2} \frac{\partial I}{\partial h} = -\frac{M}{\kappa^2 (h - z_N)^2} \frac{\partial \kappa}{\partial h} \quad (10)$$

where κ is the curvature of the beam under a moment M, δκ is the variation of the curvature by adding the extra layer. From the evaluation of E(h), the new values of A, B and D can be computed.

Residual Stresses

During the processing, the deformation of the plate is characterized by the curvature, κ(h), and the strain at z=0, $\epsilon_o(h)$. These two values can be measured using optical methods and strain gauges. In the present paper, we define the first derivative of a function f(h) of the variable h as $f^1 = \delta f/\delta h$.
deformation of the beam.

From small deformation theory, the total in-plane strain at the position z is equal to $\epsilon(z) = \epsilon_o + \kappa z$. The in-plane stress, $\sigma = \sigma_{xx} = \sigma_{yy}$ for axisymmetric conditions, is given by $$\sigma(h,z) = E_{Bi}(z)(\epsilon - \epsilon^{inel}) = E_{Bi}(z)(\epsilon_o(h) - \epsilon^{inel}(z) + (\kappa(h) - \kappa_s)z) \quad (11)$$

where $\epsilon^{inel}$ is the inelastic strain associated to the mismatch strain during processing and $\kappa_s$ is the starting curvature before deposition. For the moment, we assume that the inelastic strain depends only on z and is fixed in time. This assumption excludes a problem where we consider variation of the inelastic strain due to local thermal variation or plastic yielding. If needed, the thermal variation can be treated separately and added to the solution later.

It is important to note that

σ and ε are functions of z and h,

A, B, D, $z_N$, $I_E$, λ, κ, and $\epsilon_o$ are functions of h only, and $\epsilon^{inel}$ and $E_{Bi}$ are functions of z only.

We assume slow growth to neglect any inertia effects. For any height, h, the force and moment balances are given by $$\int_0^h \sigma dz = 0 \text{ and } \int_0^h z\sigma dz. \quad (12)$$

By differentiating Eqs. 12 with respect to h, we find that the strain mismatch at the surface (z=h) is $$\epsilon^{inel}(h) = \epsilon_o + h \quad (13)$$

By combining Eqs. 11 and 12 and differentiating with respect to h, we deduce a relation between the first differential of $\epsilon_o$ and κ given by $$\epsilon'_o(hA - B) + \kappa'(hB - D) = 0 \text{ or } \epsilon'_o + \kappa'(z_N - \lambda) = 0. \quad (14)$$

For convenience we define the function g(h) as $g(h) = z_N(h) - \lambda(h)$ and the function f(h) as f(h)=1/g(h).

$$g(h) = z_N(h) - \lambda(h) = \frac{hB - D}{hA - B} \quad (15)$$

The function $\epsilon'_o$ or κ' can be integrated from the initial conditions, $\epsilon_o h_s = 0$ taken as a reference, and $\kappa(h_s) = \kappa_s$.

$$\epsilon_0(h) = -g(h)[\kappa(h) - \kappa_s] + \int_{h_s}^h g'(\eta)[\kappa(\eta) - \kappa_s]d\eta \quad (16)$$

$$\kappa(h) - \kappa_s = -\epsilon_o(h)f(h) + \int_{h_s}^{hf} f'(\eta)\epsilon_o(\eta)d\eta \quad (17)$$

From the differentiation of Eqs. 12 and Eq. 17, the inelastic strain, $\epsilon^{inel}$, can be computed from the curvature history, κ(h), or from the strain history, $\epsilon_o(h)$. The strain mismatch in reference to the initial state of the system is equal to $$\epsilon^{inel}(h) = c_1 h(\kappa - \kappa_s) + c_2 h^2 \kappa' + \int_{h_s}^h c_3(\eta)[\kappa(\eta) - \kappa_s]d\eta \quad (18)$$

$$\epsilon^{inel}(h) = d_1 \epsilon_o + d_2 h \epsilon'_0 + \frac{1}{h}\int_{h_s}^h d_3(\eta)\epsilon_o(\eta)d\eta \quad (19)$$

where $c_i$ and $d_i$ are dimensionless function of the height h expressed as $$c_1(h) = 1 - \frac{g(h)}{h} = \frac{D - 2hB + h^2 A}{h(hA - B)} \quad (20)$$

$$c_2(h) = \frac{A}{E_{Bi}(h)} \lambda = \frac{DA - B^2}{h^2 E_{Bi}(h)(hA - B)} \quad (21)$$

-continued $$c_3(h) = g'(h) = \frac{\lambda}{h - z_N} = \frac{DA - B^2}{(hA - B)^2} \quad (22)$$

$$d_1(h) = 1 - hf(h) = 1 - \frac{h}{g(h)} = \frac{D - 2hB + h^2A}{hB - D} \quad (23)$$

$$d_2(h) = hc_2(h)f(h) = \frac{A}{E_{Bi}(h)} \frac{\lambda}{g(h)} = \frac{DA - B^2}{E_{Bi}(h)(hB - D)} \quad (24)$$

$$d_3(h) = h^2 f'(h) = h^2 \frac{DA - B^2}{(hB - D)^2} \quad (25)$$

It is interesting to note that the stress at the surface, $\sigma_s(h)$ is simply given by $$\sigma_s(h) = -A\lambda\kappa' = -\frac{I_E}{h - z_N} \kappa' = \frac{AD - B^2}{hA - B} \kappa' \quad (26)$$

$$= A\lambda f(h)\epsilon'_o = \frac{AD - B^2}{hB - D} \epsilon'_o \quad (27)$$

and the differential of the stress with respect to h at the location z is equal to $$\sigma'(z, h) = \frac{\partial \sigma}{\partial h} = E_{Bi}(z)(z - g(h))\kappa' \quad (28)$$

$$= E_{Bi}(z)(f(h)z - 1)\epsilon'_o \quad (29)$$

At any position z larger than $h_s$, the previous equation can be integrated to give the stress $$\sigma(z, h) = \sigma_S(z) - E_{Bi}(z)\left[(z - g(h))(\kappa(h) - \kappa_s) + \int_{h_s}^{h} g'(\eta)[\kappa(\eta) - \kappa_s]d\eta\right] \quad (30)$$

$$= \sigma_S(z) + E_{Bi}(z)\left[(zf(h) - 1)\epsilon_o + \int_{h_s}^{h} f'(\eta)\epsilon_o(\eta)d\eta\right]$$

where $\sigma(z, h_s)$ is the initial stress at the height z and $\kappa_s$ is the initial curvature. For the positions z small than $h_s$ (below the initial plane), the stress is given by $$\sigma(z, h) = \sigma(z, h_s) - E_{Bi}(z)\left[(z - g(h))(\kappa(h) - \kappa_s) + \int_{h_s}^{h} g'(\eta)[\kappa(\eta) - \kappa_s]d\eta\right] \quad (31)$$

$$= \sigma(z, h_s) + E_{Bi}(z)\left[(zf(h) - 1)\epsilon_o + \int_{h_s}^{h} f'(\eta)\epsilon_o(\eta)d\eta\right] \quad (32)$$

where $\sigma(z, h_s)$ is the initial stress before growth.

The function and advantage of these and other embodiments of the present invention will be more fully understood from the examples below. The following examples are intended to illustrate the benefits of the present invention, but do not exemplify the full scope of the invention.

EXAMPLES 1–28

Stress Investigation of Thin Plasma-Sprayed, Graded Ni/Al$_2$O$_3$ Multi-layered Structures In Examples 1–28, a variety of layered Ni/Al$_2$O$_3$ structures were prepared on plain carbon SAE 1010 cold-rolled steel substrates, curvature of each substrate was measured prior to and after deposition, and residual stress in each layer was determined.

For the experimental measurement, a TENCOR instrument FLX-2900 (Mountain View, Calif.) was used.

Number 29 steel substrates were polished and pre-measured using the Tencor instrument prior to deposition. No sand blasting was done on the substrates in order to avoid introducing residual stresses and residual curvature before deposition.

The deposited films were either Ni, Al$_2$O$_3$, or a combination of various volume fractions of each. Table 1 identifies the composition of the deposited layers. Examples 1–10 each included a steel substrate and an individual, approximately 100 micron-thick, homogeneous layer of Ni, Al$_2$O$_3$, or a combination. Table 1 sets forth the percent, by volume, Al$_2$O$_3$ in each of the films. In Examples 11–19, a two-layer structure was prepared on each of nine steel substrates. In each case, the first film (on the substrate) comprised a homogeneous film as in the films of Examples 1–10, respectively, and a second film on the first film comprised a homogeneous composition composed of an additional ten volume percent Al$_2$O$_3$ relative to the first film. Table 1 sets forth the composition of each of the two films of the bilayer samples of Examples 11–19. For Examples 20–28, each sample included a steel substrate and, on each substrate, a plurality of films of Ni, Al$_2$O$_3$, or a combination, each successive film of each sample containing an additional ten volume percent Al$_2$O$_3$ relative to the preceding film, and each sample including one more layer (film) relative to the preceding sample. That is, Example 20 is a three-layer structure involving a steel substrate and two deposited layers. Example 21 is a four-layer structure involving a steel substrate and three deposited layers, the first two deposited layers being identical to the two deposited layers of Example 3 and the topmost deposited layer composed of a homogeneous mixture of Ni/Al$_2$O$_3$ having an additional ten volume percent Al$_2$O$_3$ relative to the second deposited layer, etc. The samples of Examples 20–28 all were subjected to a single deposition protocol resulting in creation of the sample having the most layers, with periodic removal of each sample (except the sample having all layers) at a stage in the process appropriate for creation of that sample. Table 1 sets forth the composition of each of Examples 20–28.

After plasma spray deposition of the films, the deflection of each sample was measured and compared to the initial deflection before deposition. From the difference in deflection, the curvature of each sample could be measured and interpreted as residual stresses in the coating layers.

Figure 7:
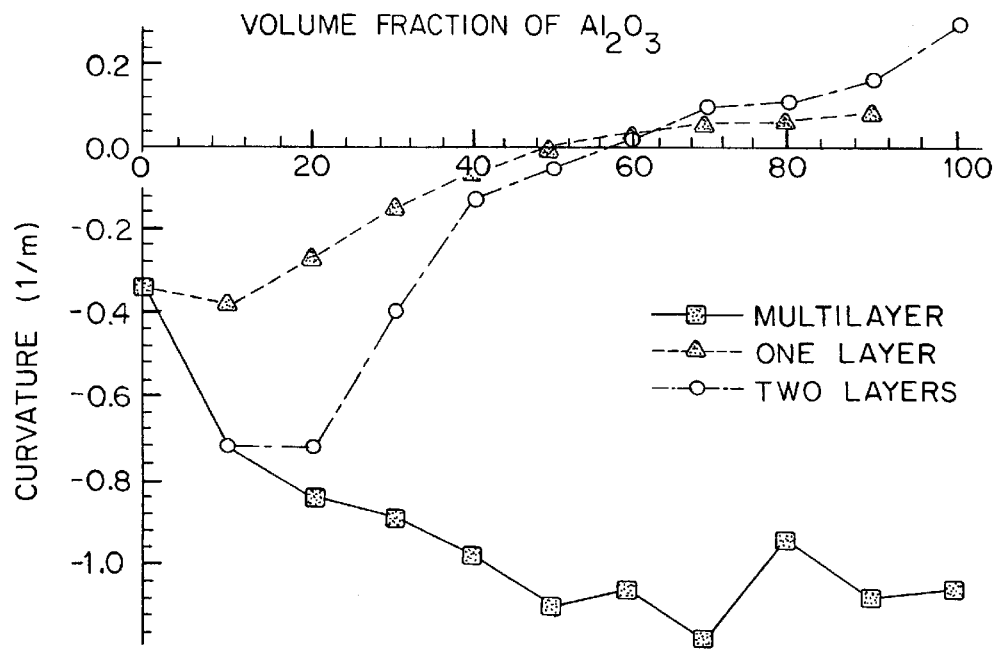
FIG. 7 plots variation of curvature of a variety of single-layer, bi-layer, and multilayered samples after deposition of plasma-sprayed $Ni/Al_2O_3$ coatings on a steel substrate, as a function of volume fraction of $Al_2O_3$ in the topmost layer.

FIG. 7 plots variation of curvature of each steel substrate of each of Examples 1–28 following deposition, relative to the curvature of the substrate prior to deposition. The "one-layer" plot represents Examples 1–10, the "two-layers" plot represents Examples 11–19, and the "multi-layer" plot represents Examples 20–28. As can be seen, for all of Examples 1–19, the curvature monotonically increases from a negative value, and becomes positive at a volume fraction of greater than about 50 percent Al$_2$O$_3$. Beyond 50 percent Al$_2$O$_3$, curvature is essentially constant. For Examples 20–28, the curvature results from the residual stress in each individual film.

TABLE 1

| Example | Wt. % Al$_2$O$_3$ | | | | | | | | | | |
|---|---|---|---|---|---|---|---|---|---|---|---|
| | 0% | 10% | 20% | 30% | 40% | 50% | 60% | 70% | 80% | 90% | 100% |
| 1 | * | | | | | | | | | | |
| 2 | | * | | | | | | | | | |
| 3 | | | * | | | | | | | | |
| 4 | | | | * | | | | | | | |
| 5 | | | | | * | | | | | | |
| 6 | | | | | | * | | | | | |
| 7 | | | | | | | * | | | | |
| 8 | | | | | | | | * | | | |
| 9 | | | | | | | | | * | | |
| 10 | | | | | | | | | | * | |
| 11 | * | * | | | | | | | | | |
| 12 | | * | * | | | | | | | | |
| 13 | | | * | * | | | | | | | |
| 14 | | | | * | * | | | | | | |
| 15 | | | | | * | * | | | | | |
| 16 | | | | | | * | * | | | | |
| 17 | | | | | | | * | * | | | |
| 18 | | | | | | | | * | * | | |
| 19 | | | | | | | | | * | * | |
| 19 | | | | | | | | | | * | * |
| 20 | * | * | * | | | | | | | | |
| 21 | * | * | * | * | | | | | | | |
| 22 | * | * | * | * | * | | | | | | |
| 23 | * | * | * | * | * | * | | | | | |
| 24 | * | * | * | * | * | * | * | | | | |
| 25 | * | * | * | * | * | * | * | * | | | |
| 26 | * | * | * | * | * | * | * | * | * | | |
| 27 | * | * | * | * | * | * | * | * | * | * | |
| 28 | * | * | * | * | * | * | * | * | * | * | * |

Average stress in each film was deduced. For Examples 1–19, interpretation of curvature was relatively straightforward since coating thickness was much smaller than substrate thickness and, as is known, for a small variation in thickness, the variation of curvature of a sample can provide the value of intrinsic stress in the added layer. For Examples 20–28, in which thickness of the deposited films was not negligible, interpretation could be conducted by bending each sample and measuring curvature resulting from bending, for example using the apparatus illustrated in FIG. 2, determining average Young's modulus of each sample, and thereby determining stress of the topmost film of each sample and stress of each film at any depth in any sample (see FIGS. 3 and 4).

Figure 8:
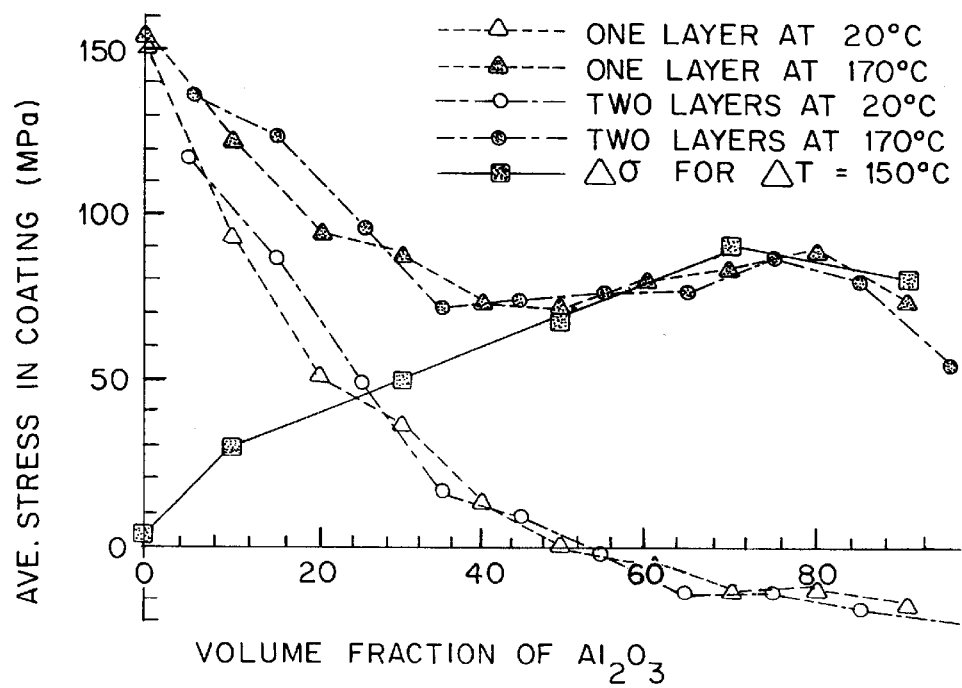
FIG. 8 plots average stress in a variety of single layer and bi-layer samples each including plasma-sprayed $Ni/Al_2O_3$ coatings on steel substrates as a function of maximum volume fraction of $Al_2O_3$ in the coatings at room temperature, the variation of stress during a 150° thermal excursion, and average stress at 170°.

The curvature of each of the samples represented by Examples 1–19 was measured at at least two temperatures, and curvature variation values of samples relative to each other were used to determine thermal mismatch between substrate and coatings, and quenching stress at processing temperatures. The results are plotted in FIG. 8. Good correlation between the "one-layer" (Examples 1–10) and "two-layer" (Examples 11–19) samples is observed. Stress was very high for low volume fraction of Al$_2$O$_3$ and decreased for increasing volume fraction of ceramic. At 50 percent Al$_2$O$_3$, the average stress was zero (noted previously by zero curvature (FIG. 7)). For higher volume fraction of Al$_2$O$_3$, stress in the coating was in compression. The stress variation for a temperature variation equal to 150° C. (represented by solid squares) shows an opposite trend, expected due to the increasing thermal mismatch between substrate and coating for increasing volume fraction of Al$_2$O$_3$. Quenching stress at the processing temperature was evaluated by summing residual stress and variation of stress with temperature. For these samples, the processing temperature was oscillated between 150° C. and 180° C. FIG. 8 represents average stress at 170° C. for the "one-layer" and "two-layer" series.

Note a decrease of quenching stress with the volume fraction of Al$_2$O$_3$ from 150 MPa for the Ni-rich layers to 50 MPa of the Al$_2$O$_3$-rich layers.

EXAMPLES 29–34

Determination of Average Stress at Room Temperature, and at Processing Temperature in Samples of Graded Ceramic Films on Steel Substrates Room Temperature Stress:

The average stress of six samples, each including a plain carbon SAE 1010 cold worked steel substrate and a film of Ni or graded Ni/Al$_2$O$_3$, was determined from curvature of each substrate due to deposition of the film, bulk properties of the steel substrate, and the thickness of the substrate and deposited film. Each graded film included a volume percent Al$_2$O$_3$ at the substrate of 0%, 20%, 40%, 60%, or 80% and gradually increased in volume percent Al$_2$O$_3$ in a direction away from the substrate to a volume percent Al$_2$O$_3$ 20% greater than that at the substrate. E.g., Example 31 was a layer on steel, including 80% Ni and 20% Al$_2$O$_3$ at the substrate and gradually changing to 60% Ni and 40% Al$_2$O$_3$ at the top of the film. The volume percent Al$_2$O$_3$ at the substrate and at the top of the film is given for each example in Table 2.

TABLE 2

| Example | vol% Al$_2$O$_3$ (substrate - top of film) |
|---|---|
| 29; 35 | (0%–0%; homogeneous Ni film) |
| 30; 36 | (0%–20%) |
| 31; 37 | (20%–40%) |
| 32; 38 | (40%–60%) |

TABLE 2-continued

| Example | vol% Al$_2$O$_3$ (substrate - top of film) |
|---|---|
| 33; 39 | (60%–80%) |
| 34; 40 | (80%–100%) |

The biaxial stiffness of the each sample beam ($I_{bi}$) was calculated using the height of the substrate+coating ($h_1$) and the Young's modulus (E) and Poisson ratio (v) of the steel substrate according to equation 33:

$$I_{bi} = \frac{h_1^3 E}{12(1-v)} \quad (33)$$

The stiffness of the beam then was used to calculate the average stress in the deposited layer, assuming that the properties of the beam are dominated by the properties of the thick steel substrate, so that the location of the neutral axis of the beam, $z_n$, is in the center of the substrate. Here, $\Delta\kappa$ is the change in curvature from a substrate with no deposit to a substrate with a coating layer deposited on it, $\Delta h$ is the change in thickness from a substrate to a substrate with a coating layer, and h is the total thickness. Equation 34 was used to determine the average stress in a single layer.

$$\sigma = \frac{I_{bi}\Delta K}{(h-z_n)\Delta h} \quad (34)$$

Figure 9:
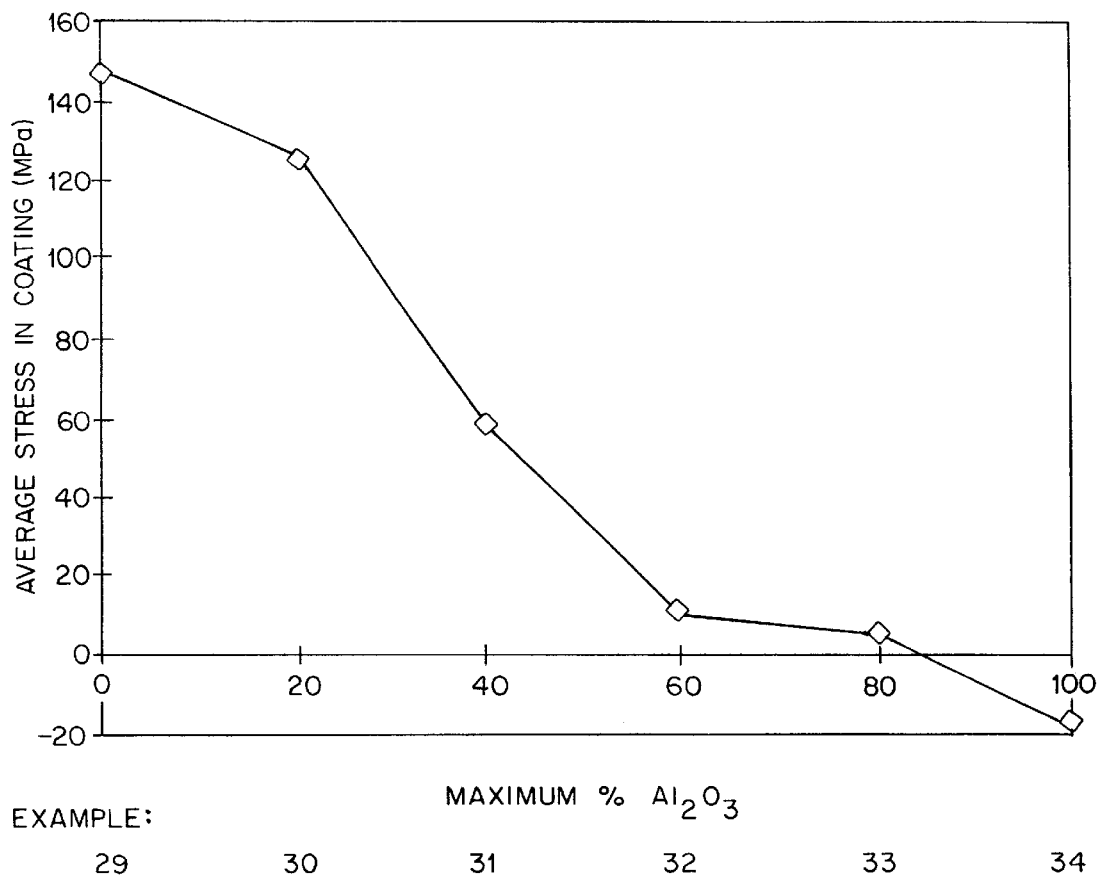
FIG. 9 plots average residual stress in a plurality of samples each including a steel substrate and a single layer of a graded coating of Ni and $Al_2O_3$.

The average stress versus maximum Al$_2$O$_3$ composition of each layer is plotted in FIG. 9, from which it can be seen that the stress in the deposited layer is tensile (positive) for each of the layers except for that which is highest in Al$_2$O$_3$ composition.

Processing Temperature Stress:

In order to separate the influence of quenching stresses from coefficient of thermal expansion mismatch stresses during cooling of the coating and substrate from the processing temperature, thermal cycling of each sample of examples 29–34 was performed. The specimens were heated to 100 degrees C. and held for one hour, then heated to 150° C. and held for an hour, and then cooled to room temperature. The measured temperature during processing was found to fluctuate from 75 to 150 degrees C. The average stress in the samples, discussed above in the Room Temperature section, was also determined at 150° C., using the thermal cycling data and equation 35, where T is temperature and all of the other symbols are as defined in equations 33 and 34.

$$\frac{\partial\sigma}{\partial T} = \frac{I_{bi}\partial^2 K}{(h-z_n)\partial h\partial T} \quad (35)$$

Figure 10:
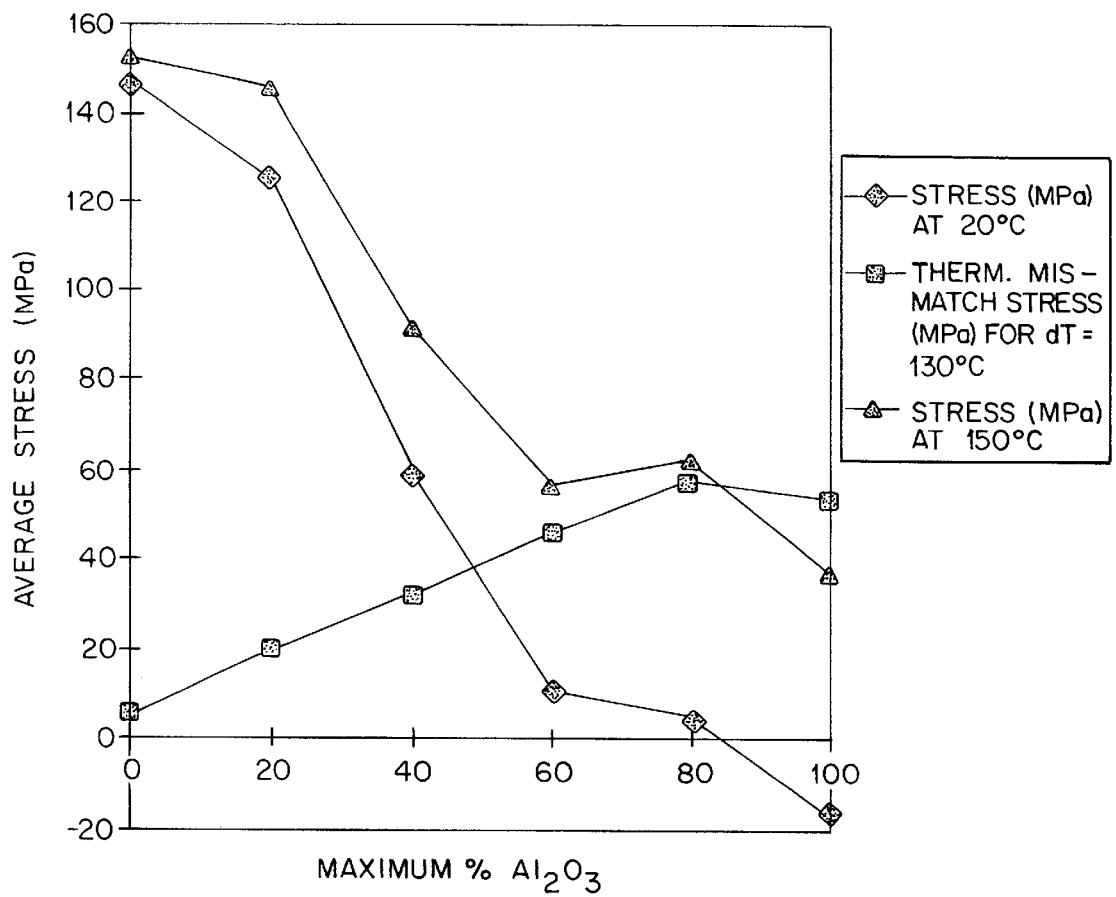
FIG. 10 plots average stress versus maximum percent $Al_2O_3$ of the samples for which data is plotted in FIG. 9 at room temperature, at 150° C., and plots thermal mismatch stress equivalent to change in residual stress upon cooling a sample to room temperature from a processing temperature.

The values of the average stress in the single layer deposits at 150° C. are plotted in FIG. 10. FIG. 10 also shows the values of stress at room temperature, and at 150 degrees C., with the difference in stress caused by the thermal mismatch and the stress due to quenching plotted separately.

EXAMPLES 35–40

Determination of Through-Thickness Coefficient of Thermal Expansion of Graded Plasma-Sprayed Ni—Al$_2$O$_3$ Coatings on Steel Substrates The average coefficient of thermal expansion of a graded coating deposited on a steel substrate was determined for six different specimens, each including a steel substrate, and a graded coating of Ni and Al$_2$O$_3$. One of the monolayer materials consisted of a single layer of nickel deposited on the steel substrate. The remaining layers were graded in 20% increments of Al$_2$O$_3$ composition, with one layer ranging from 0 to 20% Al$_2$O$_3$ in nickel, and the others ranging from 20–40%, 40–60%, 60–80%, and 80–100% Al$_2$O$_3$ in nickel. The change in curvature with temperature of each specimen was determined by thermal cycling experiments in which each specimen was heated to 150° C. while continuously measuring the curvature.

The stiffness of the beams was calculated using the values of Young's modulus, initial thickness of the substrate, thickness of the deposited layer, and neutral axis position before and after deposition according to the following relation:

$$I_1 = \frac{E\Delta h^3}{12} + E\Delta h\left(h_0 - z_{N1} + \frac{\Delta h}{2}\right)^2 + \frac{E_0 h_0^3}{12} + E_0 h_0 (z_{N0} - z_{N1})^2$$

The Young's modulus was estimated for these calculations by using a rule of mixtures, with the average value of Young's modulus for each layer being proportional to the values of Young's modulus of Ni and Al$_2$O$_3$, in proportion to their composition by volume in each specimen. In addition, the value of Young's modulus used for each of the pure materials was estimated to be one fifth of the bulk value, which are typical values observed in plasma spray deposition experiments. The composition of the samples are shown in table 2, and the calculations of CTE follow the procedure outlined previously in the theoretical background section, in equations 11–17.

Figure 11:
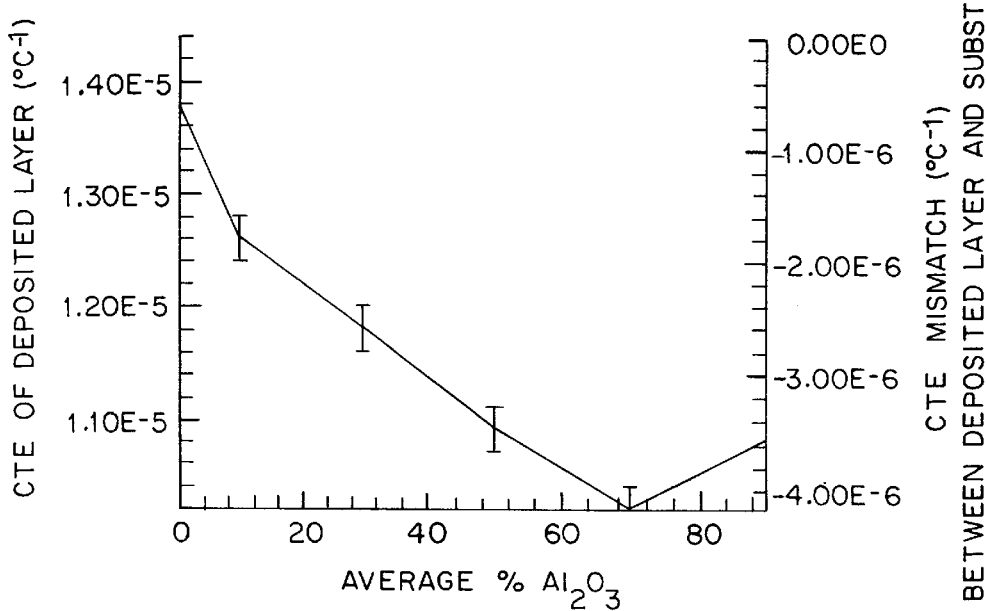
FIG. 11 plots average coefficient of thermal expansion of added layers of multi-layered samples versus average volume percent $Al_2O_3$ in each layer.

The results of these calculations are presented in FIG. 11, in which average coefficient of thermal expansion of each added layer is plotted versus average volume % Al$_2$O$_3$ in each layer. The values of CTE decrease with increasing Al$_2$O$_3$ composition, with a slight increase in value at the end resulting from the competing effects between the larger Young's modulus of Al$_2$O$_3$ over nickel and the stiffer Young's modulus of the substrate over the more porous deposited layers, combined with the usual experimental uncertainties.

Those skilled in the art will readily appreciate that all parameters listed herein are meant to be exemplary and that actual parameters will depend upon the specific application for which the methods and apparatus of the present invention are being used. It is, therefore, to be understood that the foregoing embodiments are presented by way of example only and that, within the scope of the appended claims and equivalents thereto, the invention may be practiced otherwise than as specifically described.

What is claimed is:

1. A method comprising:
    providing a first multi-layered sample including at least a first film of a first material in a first thickness and a second film of a second material in a second thickness on the first film, the second film having a first side adjacent the first film and an opposing, second side having not had additional material applied thereto;
    providing a second multi-layered sample including at least a first film of the first material in the first thickness, a second film of the second material in the second thickness on the first film, and a third film of a third material in a third thickness on the second film, the third film having a first side adjacent the second film and an opposing, second side having not had additional material applied thereto;
    providing values of stiffness, neutral axis position, and average Young's modulus of the first sample;

determining thickness of the third film;

measuring the stiffness of the second sample; and determining Young's modulus of the third film from the stiffness measurement of the second sample, the values of stiffness, neutral axis position, and average Young's modulus of the first sample, and thickness of the third film.

2. A method as in claim 1, further comprising determining average Young's modulus of the second sample.

3. A method as in claim 1, further comprising determining neutral axis position of the second sample.

4. A method as in claim 1, further comprising determining average Young's modulus and neutral axis position of the second sample.

5. A method as in claim 1, wherein the second material and the third material are the same.

6. A method as in claim 1, wherein the second material and the third material differ from each other in composition.

7. A method as in claim 6, wherein each of the first material, the second material, and the third material differ from each other in composition.

8. A method as in claim 1, wherein at least one of the second material and the third material is graded.

9. A method as in claim 1, wherein both the second material and the third material are graded.

10. A method as in claim 1, wherein the step of measuring stiffness involves applying a bending force to the second sample while directing electromagnetic radiation at a surface of the second sample and measuring an angle of deflection of the electromagnetic radiation from the surface, thereby determining curvature of the second sample due to the bending force.

11. A method as in claim 10, wherein the step of applying a bending force involves applying force in a first direction at a central location of the second sample and applying a force in a second direction opposite the first direction at each of two locations of the second sample remote from the central location.

12. A method as in claim 1, wherein the step of measuring stiffness involves applying a bending force with a four-point bending apparatus to the second sample while directing electromagnetic radiation at a surface of the second sample and measuring an angle of deflection of the electromagnetic radiation from the surface, thereby determining curvature of the second sample due to the bending force.

13. A method as in claim 1, wherein the step of providing values of stiffness, neutral axis position, and average Young's modulus of the first sample involves:

providing average Young's modulus, neutral axis position, and stiffness of the first film and thickness of the second film;

measuring the stiffness of the first sample; and determining neutral axis position and average Young's modulus of the first sample from stiffness, neutral axis position, and average Young's modulus of the first film, the stiffness of the first sample, and thickness of the second film.

14. A method as in claim 13, wherein the step of measuring stiffness involves applying a bending force to the first sample while directing electromagnetic radiation at a surface of the first sample and measuring an angle of deflection of the electromagnetic radiation from the surface, thereby determining curvature of the second sample due to the bending force.

15. A method as in claim 1, further comprising:

providing a third multi-layered sample including at least a first film of the first material in the first thickness, a second film of the second material in the second thickness on the first film, a third film of the third material in the third thickness on the second film, and a fourth film of a fourth material in a fourth thickness on the third film, the fourth film having a first side adjacent the third film and an opposing, second side having not had additional material applied thereto;

providing values of stiffness, neutral axis position, and average Young's modulus of the second sample;

determining thickness of the fourth film;

measuring the stiffness of the third sample; and determining Young's modulus of the fourth film from the stiffness measurement of the third sample, the values of stiffness, neutral axis position, and average Young's modulus of the second sample, and thickness of the fourth film.

16. A method as in claim 4, further comprising measuring a curvature variation value of the second sample relative to the first sample while a uniform temperature distribution value exists in the second sample, providing Poisson ratio of the first sample, and determining residual stress of the third film.

17. A method as in claim 4, further comprising measuring a curvature variation value of the third sample relative to the second sample while a uniform temperature distribution value exists in the third sample, providing Poisson ratio of the first sample, and determining residual stress of the third film.

18. A method as in claim 4, further comprising measuring a curvature variation value of the third sample relative to the second sample while a uniform temperature distribution value exists in the third sample, providing Poisson ratio of the first sample, and determining residual stress of the second film.

19. A method as in claim 4, further comprising measuring a curvature value of each of the first and second samples at at least two different temperatures to obtain a value of curvature variation between the first and second samples as a function of temperature;

providing average coefficient of thermal expansion and Poisson ratio of the first sample; and determining coefficient of thermal expansion of the third film.

20. A method as in claim 19, further comprising determining average coefficient of thermal expansion of the second sample.

21. A method as in claim 19, further comprising:

providing a third multi-layered sample including at least a first film of the first material in the first thickness, a second film of the second material in the second thickness on the first film, a third film of the third material in the third thickness on the second film, and a fourth film of a fourth material in a fourth thickness on the third film, the fourth film having a first side adjacent the third film and an opposing, second side having not had additional material applied thereto;

providing values of stiffness, neutral axis position, and average Young's modulus of the second sample;

determining thickness of the fourth film;

measuring the stiffness of the third sample;

determining Young's modulus of the fourth film from the stiffness measurement of the third sample, the values of stiffness, neutral axis position, and average Young's modulus of the second sample, and thickness of the fourth film;

measuring a curvature value of each of the second and third samples at at least two different temperatures to obtain a value of curvature variation between the second and third samples as a function of temperature;

providing average coefficient of thermal expansion and Poisson ratio of the second sample; and determining coefficient of thermal expansion of the fourth film.

22. A method as in claim 21, further comprising determining average coefficient of thermal expansion of the third sample.

23. A method comprising:

providing a first sample of a first film of a first material in a first thickness, having a surface;

applying a bending force to the first sample while directing electromagnetic radiation at the surface and measuring an angle of deflection of the electromagnetic radiation from the surface, thereby determining curvature of the first sample due to the applied bending force;

providing a second sample including a first film of the first material in the first thickness and a second film of a second material in a second thickness on the first film, having a surface;

applying a bending force to the second sample while directing electromagnetic radiation at the surface of the second sample and measuring an angle of deflection of the electromagnetic radiation from the surface, thereby determining curvature of the second sample due to the applied bending force;

determining stiffness of each of the first and second samples from the curvature of each sample due to bending force;

determining thickness of the second film;

providing values of neutral axis position and average Young's modulus of the first sample; and determining Young's modulus of the second film from the stiffness measurements of the first and second samples, the neutral axis position and average Young's modulus of the first sample, and thickness of the second film.

24. A method as in claim 23, wherein the step of applying a bending force involves applying force in a first direction at a central location of the first sample and applying a force in a second direction opposite the first direction at each of two locations of the first sample remote from the central location.

25. A method as in claim 23, wherein the step of applying a bending force involves applying a bending force with a four-point bending apparatus.

26. A method as in claim 23, wherein the first and second materials differ from each other in composition.

27. A method comprising:

providing a first sample created by depositing a first film of a first material in a first thickness on a substrate, the first material differing in composition from the substrate, the sample having a surface;

applying a bending force to the sample while directing electromagnetic radiation at the surface and measuring an angle of deflection of the electromagnetic radiation from the surface, thereby determining curvature of the sample due to the applied bending force;

providing values of stiffness, neutral axis position, and average Young's modulus of the substrate, determining stiffness of the first sample from the curvature of the sample due to bending force, determining thickness of the first film, and determining Young's modulus of the first film from the stiffness determination of the sample, the neutral axis position and average Young's modulus of substrate, and thickness of the first film.

28. A method as in claim 27 further comprising:

providing a second sample created by depositing a first film of the first material in the first thickness on the substrate and depositing a second film of a second material in a second thickness on first film;

providing values of stiffness, neutral axis position, and average Young's modulus of the first sample;

applying a bending force to the second sample while directing electromagnetic radiation at a surface of the second sample and measuring an angle of deflection of the electromagnetic radiation from the surface, thereby determining curvature of the second sample due to the applied bending force and stiffness of the second sample;

determining thickness of the second film; and determining Young's modulus of the second film from the stiffness measurement of the second sample, the values of stiffness, neutral axis position, and average Young's modulus of the first sample, and thickness of the second film.

29. A method as in claim 28, the second film having a first side adjacent the first film and a second, opposing side having not had material applied thereto.

30. A method as in claim 27, the first film having a first side adjacent the substrate and a second, opposing side having not had material applied thereto.

31. A method comprising:

providing values of stiffness, neutral axis position, and average Young's modulus of a first multi-layered sample including at least a first film of a first material in a first thickness and a second film of a second material in a second thickness on the first film, the second film having a first side adjacent the first film and an opposing, second side having not had additional material applied thereto;

providing a stiffness value of a second multi-layered sample including at least a first film of the first material in the first thickness, a second film of the second material in the second thickness on the first film, and a third film of a third material in a third thickness on the second film, the third film having a first side adjacent the second film and an opposing, second side having not had additional material applied thereto;

providing a value of thickness of the third film; and determining Young's modulus of the third film from the stiffness measurement of the second sample, the values of stiffness, neutral axis position, and average Young's modulus of the first sample, and thickness of the third film.

32. A method as in claim 31, further comprising determining average Young's modulus and neutral axis position of the second sample.

33. A method as in claim 31, wherein the second material and the third material differ from each other in composition.

34. A method as in claim 31, wherein the step of providing values of stiffness, neutral axis position, and average Young's modulus of the first sample involves:

providing average Young's modulus, neutral axis position, and stiffness of the first film and thickness of the second film;

measuring the stiffness of the first sample; and determining neutral axis position and average Young's modulus of the first sample from stiffness, neutral axis position, and average Young's modulus of the first film, the stiffness of the first sample, and thickness of the second film.

35. A method as in claim 34, wherein the step of measuring stiffness involves applying a bending force to the first sample while directing electromagnetic radiation at a surface of the first sample and measuring an angle of deflection of the electromagnetic radiation from the surface, thereby determining curvature of the second sample due to the bending force.

36. A method as in claim 31, further comprising:

providing values of stiffness, neutral axis position, and average Young's modulus of the second sample;

providing a stiffness value of a third multi-layered sample including at least a first film of the first material in the first thickness, a second film of the second material in the second thickness on the first film, a third film of the third material in the third thickness on the second film, and a fourth film of a fourth material in a fourth thickness on the third film, the fourth film having a first side adjacent the third film and an opposing, second side having not had additional material applied thereto;

providing a value of thickness of the fourth film; and determining Young's modulus of the fourth film from the stiffness measurement of the third sample, the values of stiffness, neutral axis position, and average Young's modulus of the second sample, and thickness of the fourth film.

37. A method comprising:

providing a first sample including at least a first film of a first material in a first thickness, the first film having a first side and an opposing, second side having not had additional material applied thereto;

providing a second, multi-layered sample including at least a first film of the first material in the first thickness and a second film of a second material in a second thickness on the first film, the second film having a first side adjacent the first film and an opposing, second side having not had additional material applied thereto;

providing values of thickness and Poisson ratio of the first sample;

providing values of stiffness, neutral axis position, and average Young's modulus of the second sample;

providing a value of Young's modulus of the second film; and measuring a curvature variation value of the second sample relative to the first sample while a uniform temperature distribution value exists in the second sample and determining residual stress of the second film.

38. A method as in claim 37, further comprising determining residual stress of the first film.

39. A method comprising:

providing a first sample including at least a first film of a first material in a first thickness, the first film having a first side and an opposing, second side having not had additional material applied thereto;

providing a second, multi-layered sample including at least a first film of the first material in the first thickness and a second film of a second material in a second thickness on the first film, the second film having a first side adjacent the first film and an opposing, second side having not had additional material applied thereto;

providing values of thickness, Poisson ratio, and average coefficient of thermal expansion of the first sample;

providing values of stiffness, neutral axis position, and average Young's modulus of the second sample;

providing a value of Young's modulus of the second film;

measuring a curvature value of each of the first and second samples at at least two different temperatures to obtain a value of curvature variation between the first and second samples as a function of temperature; and determining coefficient of thermal expansion of the second film.

40. A method as in claim 39, further comprising determining average coefficient of thermal expansion of the second sample.

* * * * *

UNITED STATES PATENT AND TRADEMARK OFFICE
CERTIFICATE OF CORRECTION

PATENT NO.         : 5,847,283
APPLICATION NO.    : 08/675121
DATED              : December 8, 1998
INVENTOR(S)        : Marc Finot et al.

Page 1 of 1

It is certified that error appears in the above-identified patent and that said Letters Patent is hereby corrected as shown below:

At column 1, line 7, please add the following:

STATEMENT REGARDING FEDERALLY SPONSORED RESEARCH OR DEVELOPMENT

At column 1, lines 7-11, "This invention was made with government support under Contract No. DE-AC07-941D13223 awarded by the U.S. Department of Energy and Grant No. N00014-94-1-0139 awarded by the Department of the Navy. The government has certain rights in the invention." should be -- This invention was made with government support under grant number N00014-94-1-0139 awarded by the Navy and grant number C95-175002 awarded by the Department of Energy. The government has certain rights in this invention. --.

Signed and Sealed this
Thirty-first Day of May, 2011

David J. Kappos
*Director of the United States Patent and Trademark Office*